US010544406B2

(12) United States Patent
Donovan et al.

(10) Patent No.: US 10,544,406 B2
(45) Date of Patent: Jan. 28, 2020

(54) CHARACTERIZATION OF FOUR PROPHAGE ENDOLYSINS SPECIFIC FOR CLOSTRIDIUM PERFRINGENS

(71) Applicants: The United States of America, as Represented by the Secretary of Agriculture, Washington, DC (US); University of Maryland, College Park, College Park, MD (US); Western University of Health Sciences, Pomona, CA (US)

(72) Inventors: David M. Donovan, Essex, MD (US); Jerel Waters, Randallstown, MD (US); Dayana T. Rowley, Beltsville, MD (US); Steven M. Swift, Bethesda, MD (US); Brian B. Oakley, Claremont, CA (US)

(73) Assignees: The United States of America, as Represented by the Secretary of Agriculture, Washington, DC (US); Western University of Health Sciences, Pamona, CA (US); University of Maryland, College Park, College Park, MD (US)

( * ) Notice: Subject to any disclaimer, the term of this patent is extended or adjusted under 35 U.S.C. 154(b) by 155 days.

(21) Appl. No.: 15/862,951

(22) Filed: Jan. 5, 2018

(65) Prior Publication Data
US 2018/0195055 A1    Jul. 12, 2018

Related U.S. Application Data

(60) Provisional application No. 62/443,375, filed on Jan. 6, 2017.

(51) Int. Cl.
| | |
|---|---|
| *C12N 9/36* | (2006.01) |
| *C12N 15/00* | (2006.01) |
| *C12N 9/24* | (2006.01) |
| *C12N 15/81* | (2006.01) |
| *A61K 38/47* | (2006.01) |
| *A61K 35/74* | (2015.01) |
| *A23K 50/75* | (2016.01) |
| *A61K 9/00* | (2006.01) |
| *A23K 20/189* | (2016.01) |
| *A61P 31/04* | (2006.01) |

(52) U.S. Cl.
CPC .......... *C12N 9/2402* (2013.01); *A23K 20/189* (2016.05); *A23K 50/75* (2016.05); *A61K 9/0053* (2013.01); *A61K 35/74* (2013.01); *A61K 38/47* (2013.01); *A61P 31/04* (2018.01); *C12N 15/81* (2013.01); *C12Y 302/01* (2013.01)

(58) Field of Classification Search
CPC .................. C12N 9/2462; C12N 15/00; C12Y 302/01017
See application file for complete search history.

(56) References Cited

PUBLICATIONS

Schmelcher et al., Current Opinion in Biotechnology, Feb. 2016, 37, 76-87.*

\* cited by examiner

*Primary Examiner* — Maryam Monshipouri
(74) *Attorney, Agent, or Firm* — John D. Fado; Maria Restrepo-Hartwig

(57) ABSTRACT

*Clostridium perfringens* can cause food poisoning and is a major agent in necrotic enteritis. As laws banning the use of antibiotics in animal feed become more common, the need for alternatives to antibiotics becomes greater. Peptidoglycan hydrolases that target the cell wall of specific bacteria are one such alternative. Genes for four endolysins, PlyCP10, PlyCP18, PlyCP33, and PlyCP41, were found within clusters of phage associated genes, likely prophages from strains Cp10, Cp18, Cp33, and Cp41. PlyCP18 and PlyCP33 harbor L-alanine amidase catalytic domains, and PlyCP10 and PlyCP41 have glycosyl hydrolase catalytic domains as predicted by BlastP and PFAM searches. All four genes were synthesized with *E. coli* codon optimization, expressed in *E. coli* expression vectors with a 6×His tag for nickel column purification, and the recombinant proteins purified. The four endolysins were capable of lysing the 66 *C. perfringens* strains tested but not the other bacteria tested.

10 Claims, 4 Drawing Sheets

Specification includes a Sequence Listing.

SEQUENCE LISTING

<160> NUMBER OF SEQ ID NOS: 18

<210> SEQ ID NO 1
<211> LENGTH: 1080
<212> TYPE: DNA
<213> ORGANISM: Clostridium perfringens

<400> SEQUENCE: 1

```
atgcagagcc gtagcgacag caacttcaag ggtatcgata ttagcaactg gcagaaaggc      60
atcaacctga accaactgaa ggagaaaggt cacgaagtgt gctatatcaa gattaccgag     120
ggtcgtggct acgttgaccc gtgctttgag gaaaactata caaggcgat tgcggcgggt     180
atgaaagtgg gcgtttacca ctattggcgt ggtaccagca gcgcgatcga acaagcgaac     240
aacattgtgc gtaccctggg cgacaagcac atcgattgca aaatcgcgat tgacgtggag     300
cagaccgatg gtctgagcta cggcgaactg aacaacagcg ttctgcaact ggcggaggaa     360
ctggagcgtc tgattggtgc ggaaatctgc atttactgca caccaactta tgcgcgtaac     420
gttctggaca gccgtctggg caagtacagc ctgtgggtgg cgcactatgg tgttaacgag     480
ccgggcgaca acccgatttg aacaaatgg gcgggtttcc agtacagcga tagcggtatc     540
agcaacgtga acggcagcct ggacctggat gagttcaccc aggaaatctt tattaacggc     600
gcgagccaaa aggcgaccga aacaaaagc ttctttacca cgcgcgtgc gaaggttgcg     660
ctggatccgc gtagcaaccc gagcgacaac tacaaagatc tgggtgaaat ctatgcggag     720
gaacgtattc aagtgctggc ggagatctgc gaccgtgaag attacctgcc ggttaagtat     780
tggaaagacg cgagcggctg cgagagcagc aaagtgtggg ttaacgcgaa caaagactac     840
ctggaaattg ataccaacgc gcgtagcttc aacatcgtga ccgagctgga tgcgcgttat     900
gaaccgagcg tgaacagcaa gcgtatgggt tacgttaaaa caacgagcg tctgtatgtg     960
caccgtgttg aaggcgacta cgttctggcg acctactatg cgggtaacgg ctacaaaacc    1020
gcgtggttta ccaaggaata tatcattaaa gatctcgagc accaccacca ccaccactga   1080
```

<210> SEQ ID NO 2
<211> LENGTH: 359
<212> TYPE: PRT
<213> ORGANISM: Clostridium perfringens

<400> SEQUENCE: 2

```
Met Gln Ser Arg Ser Asp Ser Asn Phe Lys Gly Ile Asp Ile Ser Asn
1               5                   10                  15

Trp Gln Lys Gly Ile Asn Leu Asn Gln Leu Lys Glu Lys Gly His Glu
                20                  25                  30

Val Cys Tyr Ile Lys Ile Thr Glu Gly Arg Gly Tyr Val Asp Pro Cys
            35                  40                  45

Phe Glu Glu Asn Tyr Asn Lys Ala Ile Ala Gly Met Lys Val Gly
        50                  55                  60

Val Tyr His Tyr Trp Arg Gly Thr Ser Ser Ala Ile Glu Gln Ala Asn
65                  70                  75                  80

Asn Ile Val Arg Thr Leu Gly Asp Lys His Ile Asp Cys Lys Ile Ala
                85                  90                  95

Ile Asp Val Glu Gln Thr Asp Gly Leu Ser Tyr Gly Glu Leu Asn Asn
            100                 105                 110

Ser Val Leu Gln Leu Ala Glu Glu Leu Glu Arg Leu Ile Gly Ala Glu
        115                 120                 125

Ile Cys Ile Tyr Cys Asn Thr Asn Tyr Ala Arg Asn Val Leu Asp Ser
```

```
        130                 135                 140
Arg Leu Gly Lys Tyr Ser Leu Trp Val Ala His Tyr Gly Val Asn Glu
145                 150                 155                 160

Pro Gly Asp Asn Pro Ile Trp Asn Lys Trp Ala Gly Phe Gln Tyr Ser
                165                 170                 175

Asp Ser Gly Ile Ser Asn Val Asn Gly Ser Leu Asp Leu Asp Glu Phe
            180                 185                 190

Thr Gln Glu Ile Phe Ile Asn Gly Ala Ser Gln Lys Ala Thr Glu Asn
        195                 200                 205

Lys Ser Phe Phe Thr Asn Ala Arg Ala Lys Val Ala Leu Asp Pro Arg
210                 215                 220

Ser Asn Pro Ser Asp Asn Tyr Lys Asp Leu Gly Glu Ile Tyr Ala Glu
225                 230                 235                 240

Glu Arg Ile Gln Val Leu Ala Glu Ile Cys Asp Arg Glu Asp Tyr Leu
                245                 250                 255

Pro Val Lys Tyr Trp Lys Asp Ala Ser Gly Cys Glu Ser Ser Lys Val
            260                 265                 270

Trp Val Asn Ala Asn Lys Asp Tyr Leu Glu Ile Asp Thr Asn Ala Arg
        275                 280                 285

Ser Phe Asn Ile Val Thr Glu Leu Asp Ala Arg Tyr Glu Pro Ser Val
    290                 295                 300

Asn Ser Lys Arg Met Gly Tyr Val Lys Asn Asn Glu Arg Leu Tyr Val
305                 310                 315                 320

His Arg Val Glu Gly Asp Tyr Val Leu Ala Thr Tyr Tyr Ala Gly Asn
                325                 330                 335

Gly Tyr Lys Thr Ala Trp Phe Thr Lys Glu Tyr Ile Ile Lys Asp Leu
            340                 345                 350

Glu His His His His His His
        355

<210> SEQ ID NO 3
<211> LENGTH: 954
<212> TYPE: DNA
<213> ORGANISM: Clostridium perfringens

<400> SEQUENCE: 3
atggaaatta agaaagtgta tctgaaaggc caggaagaag caaaaggttg gaacaatccg      60
aacaaaatta tcattcatca cccggaatac aatggcagca tcgaaggtct gaacaatatt     120
atgcgtaaca tgggctacta catgatcggt tacaacttct acgtgcgtaa agatggcacc     180
gtttatgaag tcgtccggt ctgggccacc ggtgcaaact gctacggtca aacaatagc      240 tctattggcg tttgtttcga gggtaactac gataaagaaa ccgaaatgcc gcaggcacaa     300
ttcaacgctg gcgtcgaact gatcgaatac ctgaaaaaca atacggcat cagcgaagca     360 aacggtcata acactatta caataccgct tgcccgggtc gttatttttcc gctggaacgc     420 atgctgaaat ctatcgatga aaacatcgtg aacgataccg acaccacgga cgttccgagt     480
tccgatgact caaacaagaa agatttctcg acgaatgcgc gtgccctggt tgcgctggat     540
ccgcgcgaca cccgagcga taattattct gacctgggcg aaatctacaa agacgaacgt     600
tttcgcgttc tggccgaagt ctgtgataag ggtgacttcc tgccgattgt gtattggaaa     660
gatagtgaag ccgtgaatc cggtaaagtg tgggttcgct caaaacagga ttatatgatg     720
atcgacacct accataaagt cttcaacgtg attacggaac tggatgcccg ttatgaaccg     780
tccccgaact catcgcgcat gggctatgtc accaatggtg aacgtctgta cgtgcaccgc     840
```

```
attgaaggca actatgcact ggctacgtac tttgcgggca atggttataa aaccgcctgg    900
ttcacgaaaa aatacatcga aaaaattctc gagcaccacc accaccacca ctga          954
```

<210> SEQ ID NO 4
<211> LENGTH: 317
<212> TYPE: PRT
<213> ORGANISM: Clostridium perfringens

<400> SEQUENCE: 4

```
Met Glu Ile Lys Lys Val Tyr Leu Lys Gly Gln Glu Ala Lys Gly
1               5                   10                  15

Trp Asn Asn Pro Asn Lys Ile Ile His His Pro Glu Tyr Asn Gly
                20                  25                  30

Ser Ile Glu Gly Leu Asn Asn Ile Met Arg Asn Met Gly Tyr Tyr Met
                35                  40                  45

Ile Gly Tyr Asn Phe Tyr Val Arg Lys Asp Gly Thr Val Tyr Glu Gly
        50                  55                  60

Arg Pro Val Trp Ala Thr Gly Ala Asn Cys Tyr Gly Gln Asn Asn Ser
65                  70                  75                  80

Ser Ile Gly Val Cys Phe Glu Gly Asn Tyr Asp Lys Glu Thr Glu Met
                85                  90                  95

Pro Gln Ala Gln Phe Asn Ala Gly Val Glu Leu Ile Glu Tyr Leu Lys
                100                 105                 110

Asn Lys Tyr Gly Ile Ser Glu Ala Asn Gly His Lys His Tyr Tyr Asn
            115                 120                 125

Thr Ala Cys Pro Gly Arg Tyr Phe Pro Leu Glu Arg Met Leu Lys Ser
    130                 135                 140

Ile Asp Glu Asn Ile Val Asn Asp Thr Asp Thr Thr Asp Val Pro Ser
145                 150                 155                 160

Ser Asp Asp Ser Asn Lys Lys Asp Phe Ser Thr Asn Ala Arg Ala Leu
                165                 170                 175

Val Ala Leu Asp Pro Arg Asp Asn Pro Ser Asp Asn Tyr Ser Asp Leu
            180                 185                 190

Gly Glu Ile Tyr Lys Asp Glu Arg Phe Arg Val Leu Ala Glu Val Cys
        195                 200                 205

Asp Lys Gly Asp Phe Leu Pro Ile Val Tyr Trp Lys Asp Ser Glu Gly
    210                 215                 220

Arg Glu Ser Gly Lys Val Trp Val Arg Ser Lys Gln Asp Tyr Met Met
225                 230                 235                 240

Ile Asp Thr Tyr His Lys Val Phe Asn Val Ile Thr Glu Leu Asp Ala
                245                 250                 255

Arg Tyr Glu Pro Ser Pro Asn Ser Ser Arg Met Gly Tyr Val Thr Asn
            260                 265                 270

Gly Glu Arg Leu Tyr Val His Arg Ile Glu Gly Asn Tyr Ala Leu Ala
        275                 280                 285

Thr Tyr Phe Ala Gly Asn Gly Tyr Lys Thr Ala Trp Phe Thr Lys Lys
    290                 295                 300

Tyr Ile Glu Lys Ile Leu Glu His His His His His His
305                 310                 315
```

<210> SEQ ID NO 5
<211> LENGTH: 954
<212> TYPE: DNA
<213> ORGANISM: Clostridium perfringens

<400> SEQUENCE: 5

```
atgcatcatc atcatcatca ctccatggaa attaagaaag tgtatctgaa aggccaggaa    60
gaagcaaaag gttggaacaa tccgaacaaa attatcattc atcacccgga atacaatggc   120
agcatcgaag gtctgaacaa tattatgcgt aacatgggct actacatgat cggttacaac   180
ttctacgtgc gtaaagatgg caccgtttat gaaggtcgtc cggtctgggc caccggtgca   240
aactgctacg gtcaaaacaa tagctctatt ggcgtttgtt tcgagggtaa ctacgataaa   300
gaaaccgaaa tgccgcaggc acaattcaac gctggcgtcg aactgatcga ataccgaaa    360
aacaaatacg gcatcagcga agcaaacggt cataaacact attacaatac cgcttgcccg   420
ggtcgttatt ttccgctgga acgcatgctg aaatctatcg atgaaaacat cgtgaacgat   480
accgacacca cggacgttcc gagttccgat gactcaaaca agaaagattt ctcgacgaat   540
gcgcgtgccc tggttgcgct ggatccgcgc gacaacccga gcgataatta ttctgacctg   600
ggcgaaatct acaaagacga acgttttcgc gttctggccg aagtctgtga taagggtgac   660
ttcctgccga ttgtgtattg gaaagatagt gaaggccgtg aatccggtaa agtgtgggtt   720
cgctcaaaac aggattatat gatgatcgac acctaccata agtcttcaa cgtgattacg    780
gaactggatg cccgttatga accgtccccg aactcatcgc gcatgggcta tgtcaccaat   840
ggtgaacgtc tgtacgtgca ccgcattgaa ggcaactatg cactggctac gtactttgcg   900
ggcaatggtt ataaaaccgc ctggttcacg aaaaaataca tcgaaaaaat ttaa          954
```

<210> SEQ ID NO 6
<211> LENGTH: 317
<212> TYPE: PRT
<213> ORGANISM: Clostridium perfringens

<400> SEQUENCE: 6

```
Met His His His His His Ser Met Glu Ile Lys Lys Val Tyr Leu
1               5                   10                  15

Lys Gly Gln Glu Glu Ala Lys Gly Trp Asn Asn Pro Asn Lys Ile Ile
            20                  25                  30

Ile His His Pro Glu Tyr Asn Gly Ser Ile Glu Gly Leu Asn Asn Ile
        35                  40                  45

Met Arg Asn Met Gly Tyr Tyr Met Ile Gly Tyr Asn Phe Tyr Val Arg
    50                  55                  60

Lys Asp Gly Thr Val Tyr Glu Gly Arg Pro Val Trp Ala Thr Gly Ala
65                  70                  75                  80

Asn Cys Tyr Gly Gln Asn Asn Ser Ser Ile Gly Val Cys Phe Glu Gly
                85                  90                  95

Asn Tyr Asp Lys Glu Thr Glu Met Pro Gln Ala Gln Phe Asn Ala Gly
            100                 105                 110

Val Glu Leu Ile Glu Tyr Leu Lys Asn Lys Tyr Gly Ile Ser Glu Ala
        115                 120                 125

Asn Gly His Lys His Tyr Tyr Asn Thr Ala Cys Pro Gly Arg Tyr Phe
    130                 135                 140

Pro Leu Glu Arg Met Leu Lys Ser Ile Asp Glu Asn Ile Val Asn Asp
145                 150                 155                 160

Thr Asp Thr Thr Asp Val Pro Ser Ser Asp Ser Asn Lys Lys Asp
                165                 170                 175

Phe Ser Thr Asn Ala Arg Ala Leu Val Ala Leu Asp Pro Arg Asp Asn
            180                 185                 190

Pro Ser Asp Asn Tyr Ser Asp Leu Gly Glu Ile Tyr Lys Asp Glu Arg
```

```
            195                 200                 205
Phe Arg Val Leu Ala Glu Val Cys Asp Lys Gly Asp Phe Leu Pro Ile
    210                 215                 220

Val Tyr Trp Lys Asp Ser Glu Gly Arg Glu Ser Gly Lys Val Trp Val
225                 230                 235                 240

Arg Ser Lys Gln Asp Tyr Met Met Ile Asp Thr Tyr His Lys Val Phe
                245                 250                 255

Asn Val Ile Thr Glu Leu Asp Ala Arg Tyr Glu Pro Ser Pro Asn Ser
            260                 265                 270

Ser Arg Met Gly Tyr Val Thr Asn Gly Glu Arg Leu Tyr Val His Arg
        275                 280                 285

Ile Glu Gly Asn Tyr Ala Leu Ala Thr Tyr Phe Ala Gly Asn Gly Tyr
    290                 295                 300

Lys Thr Ala Trp Phe Thr Lys Lys Tyr Ile Glu Lys Ile
305                 310                 315

<210> SEQ ID NO 7
<211> LENGTH: 1164
<212> TYPE: DNA
<213> ORGANISM: Clostridium perfringens

<400> SEQUENCE: 7
atgtacatca accagagcaa catcaagttt aacggcctga atacggcaa taacccgaac      60
aaaatcatca tccacaatgc ggaccaccccg aactgcagcg tttacgacat cgataagtgg    120
cacaagggta acggctggag cggtatcggc taccactatt tcattcgtaa ggacggtagc    180
atctggaccg ccgtccgga gaacgcgatt ggtgcgcaca ccattaacca gaacagcagc     240
agcatcggta tttgcctgga gggcgcgctg atgcgtgaaa accgacccg tgcgcaactg     300
aacagcctga acgacctgat cggtgatatt cgtaagcgtc gtggtaacct gccggtgtac    360
ggccacaaag acttcaacaa caccgattgc ccgggcaaga acttcccgct gagcgaattt    420
aaaaacaaca gctaccgtcc gaccggtggt agcagcgaaa ccgtggttag cgaaaacggt    480
ttttatacca gcaacgagga acgtaccaac gcgaccattg tgggcaaggg cgacatcgag    540
gttctggatg aaaagggtaa agtgatccag gccgtcaca ttagcagcct ggatcgtgtg      600
ttcgttctgg gtatttaccc gagccgtaac cacatcgagc tgatttatcc gggcaaggac    660
gaaaaatacc acgcgtatat cagcattgag aactacagcc gtctgagctt tgattaccac    720
atgcaatata agaacgacga tggtgtgacc tatgtttggt gggacagcaa gaacgtgaac    780
gttaaaaacc acgatgagga actgcagccg caccaaaaag cgagcccgat gtaccgtacc    840
aacggctggc tgcgtgttac cttctatcgt gcggacggta acccgagcga tggctacgtg    900
cgttatgagg tgaacagaa ggagcgtttt taccgtaagg gcaaagtggt taacgtgcgt     960
accagcctga ccgttcgtgc gggtgcgggt accaactata gcgcgatcgg tagcctggac   1020
ccgaacgaga acgttgaaat tctggagaaa accgaaggct ggtactatat cgaatacaat   1080
gcgcgtaacg agcgtaagcg tggctatgtg agcaaaaagt atattgagat tatccagctc   1140
gagcaccacc accaccacca ctga                                          1164

<210> SEQ ID NO 8
<211> LENGTH: 387
<212> TYPE: PRT
<213> ORGANISM: Clostridium perfringens

<400> SEQUENCE: 8
```

```
Met Tyr Ile Asn Gln Ser Asn Ile Lys Phe Asn Gly Leu Lys Tyr Gly
 1               5                  10                  15
Asn Asn Pro Asn Lys Ile Ile His Asn Ala Asp His Pro Asn Cys
            20                  25                  30
Ser Val Tyr Asp Ile Asp Lys Trp His Lys Gly Asn Gly Trp Ser Gly
        35                  40                  45
Ile Gly Tyr His Tyr Phe Ile Arg Lys Asp Gly Ser Ile Trp Thr Gly
 50                  55                  60
Arg Pro Glu Asn Ala Ile Gly Ala His Thr Ile Asn Gln Asn Ser Ser
 65                  70                  75                  80
Ser Ile Gly Ile Cys Leu Glu Gly Ala Leu Met Arg Glu Lys Pro Thr
                 85                  90                  95
Arg Ala Gln Leu Asn Ser Leu Asn Asp Leu Ile Gly Asp Ile Arg Lys
            100                 105                 110
Arg Arg Gly Asn Leu Pro Val Tyr Gly His Lys Asp Phe Asn Asn Thr
            115                 120                 125
Asp Cys Pro Gly Lys Asn Phe Pro Leu Ser Glu Phe Lys Asn Asn Ser
130                 135                 140
Tyr Arg Pro Thr Gly Gly Ser Ser Glu Thr Val Val Ser Glu Asn Gly
145                 150                 155                 160
Phe Tyr Thr Ser Asn Glu Glu Arg Thr Asn Ala Thr Ile Val Gly Lys
                165                 170                 175
Gly Asp Ile Glu Val Leu Asp Glu Lys Gly Lys Val Ile Gln Gly Arg
                180                 185                 190
His Ile Ser Ser Leu Asp Arg Val Phe Val Leu Gly Ile Tyr Pro Ser
                195                 200                 205
Arg Asn His Ile Glu Leu Ile Tyr Pro Gly Lys Asp Glu Lys Tyr His
210                 215                 220
Ala Tyr Ile Ser Ile Glu Asn Tyr Ser Arg Leu Ser Phe Asp Tyr His
225                 230                 235                 240
Met Gln Tyr Lys Asn Asp Asp Gly Val Thr Tyr Val Trp Trp Asp Ser
                245                 250                 255
Lys Asn Val Asn Val Lys Asn His Asp Glu Glu Leu Gln Pro His Gln
                260                 265                 270
Lys Ala Ser Pro Met Tyr Arg Thr Asn Gly Trp Leu Arg Val Thr Phe
            275                 280                 285
Tyr Arg Ala Asp Gly Asn Pro Ser Asp Gly Tyr Val Arg Tyr Glu Gly
            290                 295                 300
Glu Gln Lys Glu Arg Phe Tyr Arg Lys Gly Lys Val Val Asn Val Arg
305                 310                 315                 320
Thr Ser Leu Thr Val Arg Ala Gly Ala Gly Thr Asn Tyr Ser Ala Ile
                325                 330                 335
Gly Ser Leu Asp Pro Asn Glu Asn Val Glu Ile Leu Glu Lys Thr Glu
                340                 345                 350
Gly Trp Tyr Tyr Ile Glu Tyr Asn Ala Arg Asn Glu Arg Lys Arg Gly
                355                 360                 365
Tyr Val Ser Lys Lys Tyr Ile Glu Ile Ile Gln Leu Glu His His His
        370                 375                 380
His His His
385

<210> SEQ ID NO 9
<211> LENGTH: 1032
<212> TYPE: DNA
```

<213> ORGANISM: Clostridium perfringens

<400> SEQUENCE: 9

```
atgctgaagg gtatcgacgt tagcgagcac cagggccgta ttgattggga acgtgtgaag      60
ggtaacatcg acttcgcgat tctgcgtgcg ggttacggcc gtaacaacat cgataagcaa     120
tttatccgta acattgagga atgcaaccgt ctgtgcatcc cggttggtat ttactggttc     180
agctatgcgt ggaacgagga atggcgaag aacgaggcgc gttacgttct ggaagcgatc      240
aaaggctacc gtgtggacta tccgattagc tacgacctgg aatatgatac cctgaactat     300
gcgagcaaga acggtgttac catcggcaaa cgtctggcga ccgacatggt gaaagcgttt     360
tgcgatgaaa ttaaccgtaa cggttaccgt gcgatgaact ataccaacca ggatttcctg     420
ctgaacaagt tttacatgaa cgagctgacc aactatccgc tgtggtacgc gtggtataac     480
agcaaactga ccgtgattg cgcgatctgg cagtacagcg agagcggtca agttccgggc      540
attggtggcg cgagcgtgga catgaactac tgctatgagg acttcctgaa gaaagatttt     600
accctggaaa acgcgaccac ctgcaacgtt gataccgagc tgaacatccg tgcgaagggt     660
accaccggcg cgaccatcgt tggtagcatt ccggcgggcg accgtttccg tattaaatgg     720
gtggacagcg attacctggg ttggtactat atcgaatatc aaggtattac cggctacgtt     780
agccaggatt atgtggagaa gctgcaaatg cgaccacct gcaacgtgga cagcgttctg      840
aacgtgcgtg cggagggtaa caccagcagc aacatcgtgg cgaccattaa cccgggcgag     900
gttttccgta tcgattgggt ggacagcgat tttatcggct ggtaccgtat taccaccgcg     960
aacggtgcga acggcttcgt taaaagcgac tttgtgaaga actgctcga gcaccaccac    1020
caccaccact ga                                                       1032
```

<210> SEQ ID NO 10
<211> LENGTH: 343
<212> TYPE: PRT
<213> ORGANISM: Clostridium perfringens

<400> SEQUENCE: 10

```
Met Leu Lys Gly Ile Asp Val Ser Glu His Gln Gly Arg Ile Asp Trp
 1               5                  10                  15

Glu Arg Val Lys Gly Asn Ile Asp Phe Ala Ile Leu Arg Ala Gly Tyr
             20                  25                  30

Gly Arg Asn Asn Ile Asp Lys Gln Phe Ile Arg Asn Ile Glu Glu Cys
         35                  40                  45

Asn Arg Leu Cys Ile Pro Val Gly Ile Tyr Trp Phe Ser Tyr Ala Trp
     50                  55                  60

Asn Glu Glu Met Ala Lys Asn Glu Ala Arg Tyr Val Leu Glu Ala Ile
 65                  70                  75                  80

Lys Gly Tyr Arg Val Asp Tyr Pro Ile Ser Tyr Asp Leu Glu Tyr Asp
                 85                  90                  95

Thr Leu Asn Tyr Ala Ser Lys Asn Gly Val Thr Ile Gly Lys Arg Leu
            100                 105                 110

Ala Thr Asp Met Val Lys Ala Phe Cys Asp Glu Ile Asn Arg Asn Gly
        115                 120                 125

Tyr Arg Ala Met Asn Tyr Thr Asn Gln Asp Phe Leu Leu Asn Lys Phe
    130                 135                 140

Tyr Met Asn Glu Leu Thr Asn Tyr Pro Leu Trp Tyr Ala Trp Tyr Asn
145                 150                 155                 160

Ser Lys Leu Asn Arg Asp Cys Ala Ile Trp Gln Tyr Ser Glu Ser Gly
```

```
                165                 170                 175
Gln Val Pro Gly Ile Gly Gly Ala Ser Val Asp Met Asn Tyr Cys Tyr
            180                 185                 190

Glu Asp Phe Leu Lys Lys Asp Phe Thr Leu Glu Asn Ala Thr Thr Cys
            195                 200                 205

Asn Val Asp Thr Glu Leu Asn Ile Arg Ala Lys Gly Thr Thr Gly Ala
    210                 215                 220

Thr Ile Val Gly Ser Ile Pro Ala Gly Asp Arg Phe Arg Ile Lys Trp
225                 230                 235                 240

Val Asp Ser Asp Tyr Leu Gly Trp Tyr Tyr Ile Glu Tyr Gln Gly Ile
                245                 250                 255

Thr Gly Tyr Val Ser Gln Asp Tyr Val Glu Lys Leu Gln Met Ala Thr
            260                 265                 270

Thr Cys Asn Val Asp Ser Val Leu Asn Val Arg Ala Glu Gly Asn Thr
            275                 280                 285

Ser Ser Asn Ile Val Ala Thr Ile Asn Pro Gly Glu Val Phe Arg Ile
        290                 295                 300

Asp Trp Val Asp Ser Asp Phe Ile Gly Trp Tyr Arg Ile Thr Thr Ala
305                 310                 315                 320

Asn Gly Ala Asn Gly Phe Val Lys Ser Asp Phe Val Lys Lys Leu Leu
                325                 330                 335

Glu His His His His His His
            340

<210> SEQ ID NO 11
<211> LENGTH: 1056
<212> TYPE: DNA
<213> ORGANISM: Clostridium perfringens

<400> SEQUENCE: 11
atgcaaagta gaagtgatag taattttaaa ggaatagaca taagtaactg gcaaaaaggt      60
attaatttaa atcaattaaa agaaaaagga catgaagttt gttatattaa aattacagaa     120
ggaagaggat atgtagatcc atgctttgaa gaaaattata taaaagcaat agcagcagga     180
atgaaagtag agtttatca ttattggaga ggtacttcaa gtgctataga acaggctaat      240
aacatagtta gaactttagg ggataaacat attgattgta aaatagcaat agatgtggag     300
caaactgatg gattaagtta tggagaatta ataatagtg ttcttcaatt agcagaagaa      360
ttagaaagat aataggagc tgagatttgt atttattgta atacaaacta tgctagaaat      420
gtattagata gcagattagg taagtattca ttatgggtag ctcattatgg agtaaatgaa     480
ccaggagata tcctatatg gaataaatgg gcaggattcc aatattcaga tagtggaatt      540
tcaaatgtaa atgaagtttt agatttagat gaatttacac aagaaatttt tattaatgga     600
gcaagtcaaa aagcaactga aaataaatca ttttttacaa atgcaagagc aaaggtagca     660
ttagacccaa gaagcaatcc gagtgataac tacaaagact taggagaaat atatgcagag     720
gaaagaatac aagtattagc agagatttgt gatagagaag attacttacc agttaagtat     780
tggaaagatg catcaggatg tgaaagttca aaggtttggg taaatgcaaa taaggattac     840
ttagagatag atactaatgc tagatcattt aatatagtta cagagcttga tgctagatat     900
gagccatcag ttaactcaaa gagaatgggg tatgtaaaaa ataatgaaag attatatgtg     960
catagagtag aaggagatta tgttttagca acatactatg caggaaatgg atataaaact    1020
gcttggttta caaagaata tataattaaa gattaa                               1056
```

<210> SEQ ID NO 12
<211> LENGTH: 351
<212> TYPE: PRT
<213> ORGANISM: Clostridium perfringens

<400> SEQUENCE: 12

Met Gln Ser Arg Ser Asp Ser Asn Phe Lys Gly Ile Asp Ile Ser Asn
1               5                   10                  15

Trp Gln Lys Gly Ile Asn Leu Asn Gln Leu Lys Glu Lys Gly His Glu
            20                  25                  30

Val Cys Tyr Ile Lys Ile Thr Glu Gly Arg Gly Tyr Val Asp Pro Cys
        35                  40                  45

Phe Glu Glu Asn Tyr Asn Lys Ala Ile Ala Ala Gly Met Lys Val Gly
    50                  55                  60

Val Tyr His Tyr Trp Arg Gly Thr Ser Ala Ile Glu Gln Ala Asn
65                  70                  75                  80

Asn Ile Val Arg Thr Leu Gly Asp Lys His Ile Asp Cys Lys Ile Ala
                85                  90                  95

Ile Asp Val Glu Gln Thr Asp Gly Leu Ser Tyr Gly Glu Leu Asn Asn
            100                 105                 110

Ser Val Leu Gln Leu Ala Glu Glu Leu Glu Arg Leu Ile Gly Ala Glu
        115                 120                 125

Ile Cys Ile Tyr Cys Asn Thr Asn Tyr Ala Arg Asn Val Leu Asp Ser
    130                 135                 140

Arg Leu Gly Lys Tyr Ser Leu Trp Val Ala His Tyr Gly Val Asn Glu
145                 150                 155                 160

Pro Gly Asp Asn Pro Ile Trp Asn Lys Trp Ala Gly Phe Gln Tyr Ser
                165                 170                 175

Asp Ser Gly Ile Ser Asn Val Asn Gly Ser Leu Asp Leu Asp Glu Phe
            180                 185                 190

Thr Gln Glu Ile Phe Ile Asn Gly Ala Ser Gln Lys Ala Thr Glu Asn
        195                 200                 205

Lys Ser Phe Phe Thr Asn Ala Arg Ala Lys Val Ala Leu Asp Pro Arg
    210                 215                 220

Ser Asn Pro Ser Asp Asn Tyr Lys Asp Leu Gly Glu Ile Tyr Ala Glu
225                 230                 235                 240

Glu Arg Ile Gln Val Leu Ala Glu Ile Cys Asp Arg Glu Asp Tyr Leu
                245                 250                 255

Pro Val Lys Tyr Trp Lys Asp Ala Ser Gly Cys Glu Ser Ser Lys Val
            260                 265                 270

Trp Val Asn Ala Asn Lys Asp Tyr Leu Glu Ile Asp Thr Asn Ala Arg
        275                 280                 285

Ser Phe Asn Ile Val Thr Glu Leu Asp Ala Arg Tyr Glu Pro Ser Val
    290                 295                 300

Asn Ser Lys Arg Met Gly Tyr Val Lys Asn Asn Glu Arg Leu Tyr Val
305                 310                 315                 320

His Arg Val Glu Gly Asp Tyr Val Leu Ala Thr Tyr Ala Gly Asn
                325                 330                 335

Gly Tyr Lys Thr Ala Trp Phe Thr Lys Glu Tyr Ile Ile Lys Asp
            340                 345                 350

<210> SEQ ID NO 13
<211> LENGTH: 930
<212> TYPE: DNA
<213> ORGANISM: Clostridium perfringens

<400> SEQUENCE: 13

```
atggaaatta aaaagtata tttaaaagga caagaagaag ctaaaggatg gaataatcca      60
aataaaataa taattcacca tccagagtac aatggatcta tagaaggatt aaataatata     120
atgagaaata tgggatatta catgataggg tataacttct acgtacgtaa agatggtaca    180
gtatatgaag gtagaccagt atgggcaaca ggagctaatt gttatggtca aaataactct    240
tcaataggtg tgtgctttga aggtaattac gataaagaaa ctgaaatgcc acaagctcaa    300
tttaatgctg gcgtagagct tatagagtat ttaaaaaaca aatatggaat tagtgaagct    360
aatggacata agcactatta taatacggcg tgtccaggaa gatactttcc actagaaaga    420
atgttaaaat ctatagatga gaatatagta aatgatacag atactacaga tgttccttct    480
agtgatgatt ctaataaaaa agacttttct actaatgcaa gagctttagt agcgttagat    540
cctagagata acccaagtga taactatagt gatttaggag aaatttataa agatgaaaga    600
tttagagttt tagcagaagt atgtgataaa ggagattttc ttcctatagt ttattggaaa    660
gattcagaag gtagagaatc aggaaaagta tgggttagaa gtaaacaaga ttatatgatg    720
atagatactt accataaagt atttaatgtt atcacagaat tagacgctag atatgaacct    780
tctcctaatt caagtagaat gggctatgtt acaaatgggg aaagactata tgtgcataga    840
atagaaggaa attatgcact agcaacatac ttcgcaggta tgggtataaa acagcttgg     900
tttacaaaaa aatatattga aaaatataa                                       930
```

<210> SEQ ID NO 14
<211> LENGTH: 309
<212> TYPE: PRT
<213> ORGANISM: Clostridium perfringens

<400> SEQUENCE: 14

```
Met Glu Ile Lys Lys Val Tyr Leu Lys Gly Gln Glu Glu Ala Lys Gly
1               5                   10                  15

Trp Asn Asn Pro Asn Lys Ile Ile Ile His His Pro Glu Tyr Asn Gly
            20                  25                  30

Ser Ile Glu Gly Leu Asn Asn Ile Met Arg Asn Met Gly Tyr Tyr Met
        35                  40                  45

Ile Gly Tyr Asn Phe Tyr Val Arg Lys Asp Gly Thr Val Tyr Glu Gly
    50                  55                  60

Arg Pro Val Trp Ala Thr Gly Ala Asn Cys Tyr Gly Gln Asn Asn Ser
65                  70                  75                  80

Ser Ile Gly Val Cys Phe Glu Gly Asn Tyr Asp Lys Glu Thr Glu Met
                85                  90                  95

Pro Gln Ala Gln Phe Asn Ala Gly Val Glu Leu Ile Glu Tyr Leu Lys
            100                 105                 110

Asn Lys Tyr Gly Ile Ser Glu Ala Asn Gly His Lys His Tyr Tyr Asn
        115                 120                 125

Thr Ala Cys Pro Gly Arg Tyr Phe Pro Leu Glu Arg Met Leu Lys Ser
    130                 135                 140

Ile Asp Glu Asn Ile Val Asn Asp Thr Asp Thr Thr Asp Val Pro Ser
145                 150                 155                 160

Ser Asp Asp Ser Asn Lys Lys Asp Phe Ser Thr Asn Ala Arg Ala Leu
                165                 170                 175

Val Ala Leu Asp Pro Arg Asp Asn Pro Ser Asp Asn Tyr Ser Asp Leu
            180                 185                 190
```

Gly Glu Ile Tyr Lys Asp Glu Arg Phe Arg Val Leu Ala Glu Val Cys
            195                 200                 205

Asp Lys Gly Asp Phe Leu Pro Ile Val Tyr Trp Lys Asp Ser Glu Gly
    210                 215                 220

Arg Glu Ser Gly Lys Val Trp Val Arg Ser Lys Gln Asp Tyr Met Met
225                 230                 235                 240

Ile Asp Thr Tyr His Lys Val Phe Asn Val Ile Thr Glu Leu Asp Ala
                245                 250                 255

Arg Tyr Glu Pro Ser Pro Asn Ser Ser Arg Met Gly Tyr Val Thr Asn
            260                 265                 270

Gly Glu Arg Leu Tyr Val His Arg Ile Glu Gly Asn Tyr Ala Leu Ala
    275                 280                 285

Thr Tyr Phe Ala Gly Asn Gly Tyr Lys Thr Ala Trp Phe Thr Lys Lys
    290                 295                 300

Tyr Ile Glu Lys Ile
305

<210> SEQ ID NO 15
<211> LENGTH: 1140
<212> TYPE: DNA
<213> ORGANISM: Clostridium perfringens

<400> SEQUENCE: 15
atgtacatca atcaatcaaa cataaaattt aatgggttaa aatatggtaa taatcctaat        60
aaaattatta ttcataatgc agatcatcct aactgcagcg tatatgacat agataagtgg       120
cataaaggaa atggatggag tggcatagga tatcattatt ttattagaaa agatggttct       180
atatggacag gtagacctga aaatgctata ggagctcata ctataaatca aaatagttca       240
agtataggta tttgtttaga aggtgcttta atgagagaaa aaccaactag agcacaatta       300
aactctctta tgatttaat tggagatata agaaaaagaa gaggcaattt acctgtgtat       360
ggacataagg attttaataa tacagattgt ccaggaaaga acttcccatt aagtgaattc       420
aaaaacaatt catacagacc aactggcgga agttctgaaa ctgtagtatc agaaaatgga       480
ttctatacaa gcaatgaaga agaactaat gcaactatag ttggaaaagg agatatagag       540
gttttagatg aaaaaggtaa agttattcaa gggagacata tatcaagttt agacagagtt       600
tttgtactag gtatatatcc atcaagaaat catatagaac ttatttatcc aggaaaagat       660
gaaaaatatc atgcttatat ttctatagaa aactatagta gattaagttt tgattaccac       720
atgcaatata agaatgatga tggtgttacg tacgtatggt gggattcaaa aaatgttaat       780
gtaaaaaatc atgatgaaga attacaacca caccaaaaag cttcaccaat gtatagaact       840
aatggttggc tacgtgtaac attttatcgt gctgatggta atccaagtga tggctatgtt       900
cgttatgaag gagaacaaaa agaaagattt tatagaaaag gtaaagtagt aaatgttaga       960
acctctttaa ccgtaagagc aggagcagga actaactatt cagctatagg aagtttagat      1020
cctaacgaaa atgtagaaat tttagaaaaa acagaaggtt ggtactatat agaatataat      1080
gctagaaatg aaagaaaaag aggatatgta agtaaaaaat atattgaaat aattcaataa      1140

<210> SEQ ID NO 16
<211> LENGTH: 379
<212> TYPE: PRT
<213> ORGANISM: Clostridium perfringens

<400> SEQUENCE: 16

Met Tyr Ile Asn Gln Ser Asn Ile Lys Phe Asn Gly Leu Lys Tyr Gly

|   | 1 |   |   |   | 5 |   |   |   |   | 10 |   |   |   |   | 15 |   |
|---|---|---|---|---|---|---|---|---|---|---|---|---|---|---|---|---|

Asn Asn Pro Asn Lys Ile Ile Ile His Asn Ala Asp His Pro Asn Cys
                20                  25                  30

Ser Val Tyr Asp Ile Asp Lys Trp His Lys Gly Asn Gly Trp Ser Gly
            35                  40                  45

Ile Gly Tyr His Tyr Phe Ile Arg Lys Asp Gly Ser Ile Trp Thr Gly
        50                  55                  60

Arg Pro Glu Asn Ala Ile Gly Ala His Thr Ile Asn Gln Asn Ser Ser
65                  70                  75                  80

Ser Ile Gly Ile Cys Leu Glu Gly Ala Leu Met Arg Glu Lys Pro Thr
                85                  90                  95

Arg Ala Gln Leu Asn Ser Leu Asn Asp Leu Ile Gly Asp Ile Arg Lys
                100                 105                 110

Arg Arg Gly Asn Leu Pro Val Tyr Gly His Lys Asp Phe Asn Asn Thr
            115                 120                 125

Asp Cys Pro Gly Lys Asn Phe Pro Leu Ser Glu Phe Lys Asn Asn Ser
130                 135                 140

Tyr Arg Pro Thr Gly Gly Ser Ser Glu Thr Val Val Ser Glu Asn Gly
145                 150                 155                 160

Phe Tyr Thr Ser Asn Glu Glu Arg Thr Asn Ala Thr Ile Val Gly Lys
                165                 170                 175

Gly Asp Ile Glu Val Leu Asp Glu Lys Gly Lys Val Ile Gln Gly Arg
            180                 185                 190

His Ile Ser Ser Leu Asp Arg Val Phe Val Leu Gly Ile Tyr Pro Ser
        195                 200                 205

Arg Asn His Ile Glu Leu Ile Tyr Pro Gly Lys Asp Glu Lys Tyr His
210                 215                 220

Ala Tyr Ile Ser Ile Glu Asn Tyr Ser Arg Leu Ser Phe Asp Tyr His
225                 230                 235                 240

Met Gln Tyr Lys Asn Asp Asp Gly Val Thr Tyr Val Trp Trp Asp Ser
                245                 250                 255

Lys Asn Val Asn Val Lys Asn His Asp Glu Glu Leu Gln Pro His Gln
            260                 265                 270

Lys Ala Ser Pro Met Tyr Arg Thr Asn Gly Trp Leu Arg Val Thr Phe
        275                 280                 285

Tyr Arg Ala Asp Gly Asn Pro Ser Asp Gly Tyr Val Arg Tyr Glu Gly
            290                 295                 300

Glu Gln Lys Glu Arg Phe Tyr Arg Lys Gly Lys Val Val Asn Val Arg
305                 310                 315                 320

Thr Ser Leu Thr Val Arg Ala Gly Ala Gly Thr Asn Tyr Ser Ala Ile
                325                 330                 335

Gly Ser Leu Asp Pro Asn Glu Asn Val Glu Ile Leu Glu Lys Thr Glu
            340                 345                 350

Gly Trp Tyr Tyr Ile Glu Tyr Asn Ala Arg Asn Glu Arg Lys Arg Gly
        355                 360                 365

Tyr Val Ser Lys Lys Tyr Ile Glu Ile Ile Gln
370                 375

<210> SEQ ID NO 17
<211> LENGTH: 1008
<212> TYPE: DNA
<213> ORGANISM: Clostridium perfringens

<400> SEQUENCE: 17

```
atgttaaaag gaatagacgt atcagaacac caaggaagaa tagattggga aagagtaaaa    60
ggtaatatag attttgctat attaagagca ggatatggaa gaaataatat agataagcaa   120
tttataagaa atatagaaga gtgtaataga ttatgtattc cagtaggtat atattggttt   180
agttatgctt ggaatgaaga aatggctaag aatgaagcta gatatgtgct agaagccatt   240
aaaggttata gagttgatta tcctataagc tatgacctag aatatgatac tttaaactat   300
gcatctaaaa atggagttac tataggaaaa agattagcta cagatatggt taaagccttt   360
tgtgatgaaa taaaccgtaa cggatataga gctatgaact atactaacca agatttctta   420
ttaaataaat tctatatgaa tgagttaact aattatccat tatggtatgc atggtataac   480
tctaaactta atagagattg tgctatatgg caatattcag aaagtggaca agtaccaggc   540
attggtggag caagcgtaga tatgaactat tgctatgaag atttcttaaa gaaagatttt   600
acactagaaa atgctactac ttgtaatgtc gatactgaat aaatataag agcaaaagga   660 actacaggtg caactatagt cggaagcata cctgcaggag atagatttag aattaagtgg   720
gtagattctg attacttagg ttggtattac atagagtacc aaggtattac tggatatgta   780
agccaagact atgtagaaaa acttcaaatg gctactactt gcaatgtaga ttcagttctt   840
aatgttagag cagaaggtaa tacaagttct aatatagtag ctacaattaa tccaggagaa   900
gtattcagaa tagattgggt agattcagac tttattggct ggtatagaat tactacagct   960
aatggagcaa atggatttgt taaatcagat tttgtaaaga aactataa               1008
```

<210> SEQ ID NO 18
<211> LENGTH: 335
<212> TYPE: PRT
<213> ORGANISM: Clostridium perfringens

<400> SEQUENCE: 18

```
Met Leu Lys Gly Ile Asp Val Ser Glu His Gln Gly Arg Ile Asp Trp
1               5                   10                  15

Glu Arg Val Lys Gly Asn Ile Asp Phe Ala Ile Leu Arg Ala Gly Tyr
            20                  25                  30

Gly Arg Asn Asn Ile Asp Lys Gln Phe Ile Arg Asn Ile Glu Glu Cys
        35                  40                  45

Asn Arg Leu Cys Ile Pro Val Gly Ile Tyr Trp Phe Ser Tyr Ala Trp
    50                  55                  60

Asn Glu Glu Met Ala Lys Asn Glu Ala Arg Tyr Val Leu Glu Ala Ile
65                  70                  75                  80

Lys Gly Tyr Arg Val Asp Tyr Pro Ile Ser Tyr Asp Leu Glu Tyr Asp
                85                  90                  95

Thr Leu Asn Tyr Ala Ser Lys Asn Gly Val Thr Ile Gly Lys Arg Leu
            100                 105                 110

Ala Thr Asp Met Val Lys Ala Phe Cys Asp Glu Ile Asn Arg Asn Gly
        115                 120                 125

Tyr Arg Ala Met Asn Tyr Thr Asn Gln Asp Phe Leu Leu Asn Lys Phe
    130                 135                 140

Tyr Met Asn Glu Leu Thr Asn Tyr Pro Leu Trp Tyr Ala Trp Tyr Asn
145                 150                 155                 160

Ser Lys Leu Asn Arg Asp Cys Ala Ile Trp Gln Tyr Ser Glu Ser Gly
                165                 170                 175

Gln Val Pro Gly Ile Gly Gly Ala Ser Val Asp Met Asn Tyr Cys Tyr
            180                 185                 190

Glu Asp Phe Leu Lys Lys Asp Phe Thr Leu Glu Asn Ala Thr Thr Cys
```

|     |     |     |     |     | 195 |     |     |     |     | 200 |     |     |     |     | 205 |     |     |
| --- | --- | --- | --- | --- | --- | --- | --- | --- | --- | --- | --- | --- | --- | --- | --- | --- | --- |
| Asn | Val | Asp | Thr | Glu | Leu | Asn | Ile | Arg | Ala | Lys | Gly | Thr | Thr | Gly | Ala |
|     | 210 |     |     |     |     | 215 |     |     |     | 220 |     |     |     |     |     |
| Thr | Ile | Val | Gly | Ser | Ile | Pro | Ala | Gly | Asp | Arg | Phe | Arg | Ile | Lys | Trp |
| 225 |     |     |     |     | 230 |     |     |     |     | 235 |     |     |     |     | 240 |
| Val | Asp | Ser | Asp | Tyr | Leu | Gly | Trp | Tyr | Tyr | Ile | Glu | Tyr | Gln | Gly | Ile |
|     |     |     |     | 245 |     |     |     |     | 250 |     |     |     |     | 255 |     |
| Thr | Gly | Tyr | Val | Ser | Gln | Asp | Tyr | Val | Glu | Lys | Leu | Gln | Met | Ala | Thr |
|     |     |     | 260 |     |     |     |     | 265 |     |     |     |     | 270 |     |     |
| Thr | Cys | Asn | Val | Asp | Ser | Val | Leu | Asn | Val | Arg | Ala | Glu | Gly | Asn | Thr |
|     |     | 275 |     |     |     |     | 280 |     |     |     |     | 285 |     |     |     |
| Ser | Ser | Asn | Ile | Val | Ala | Thr | Ile | Asn | Pro | Gly | Glu | Val | Phe | Arg | Ile |
|     | 290 |     |     |     |     | 295 |     |     |     |     | 300 |     |     |     |     |
| Asp | Trp | Val | Asp | Ser | Asp | Phe | Ile | Gly | Trp | Tyr | Arg | Ile | Thr | Thr | Ala |
| 305 |     |     |     |     | 310 |     |     |     |     | 315 |     |     |     |     | 320 |
| Asn | Gly | Ala | Asn | Gly | Phe | Val | Lys | Ser | Asp | Phe | Val | Lys | Lys | Leu |     |
|     |     |     |     | 325 |     |     |     |     | 330 |     |     |     |     | 335 |     |

CHARACTERIZATION OF FOUR PROPHAGE ENDOLYSINS SPECIFIC FOR CLOSTRIDIUM PERFRINGENS

CROSS-REFERENCE

The present application claims priority to U.S. Provisional Patent Application Ser. No. 62/443,375 filed Jan. 6, 2017, the content of which is expressly incorporated herein by reference.

BACKGROUND OF THE INVENTION

This invention relates to nucleic acid molecules encoding the phage endolysins: PlyCP10, PlyCP18, PlyCP33, and PlyCP41, PlyCP18 and PlyCP33 harbor L-alanine amidase catalytic domains, and PlyCP10 and PlyCP41 have glycosyl hydrolase catalytic domains which specifically attack the peptidoglycan cell wall of *Clostridium perfringens* bacteria which contributes to severe gut infections (necrotic enteritis) in animals such as poultry, and new-born cattle and swine.

*Clostridium perfringens* is a Gram-positive, spore forming, anaerobic bacterium commonly present in the intestines of humans and animals. *C. perfringens* is classified into one of five types (A, B, C, D, or E) based on the toxin production. Spores of the pathogen can persist in soil, feces or the environment, and the bacterium causes many severe infections of animals and humans. Some strains of *C. perfringens* type A produce an enterotoxin (CPE) during sporulation that are responsible for food-borne disease in humans (Smedley et al. 2004. *Rev. Physiol. Bioch. P.* 152:183-204; Sawires and Songer. 2006. *Anaerobe* 12:23-43; Scallan et al. 2011. *Emerg. Infect. Dis.* 17:16-22). *C. perfringens* can cause food poisoning, gas gangrene, necrotic enteritis, and non-foodborne gastrointestinal infections in humans.

Necrotic enteritis is a peracute disease syndrome and is the most common and financially devastating bacterial disease in modern broiler flocks. The clinical form in poultry is caused by alpha toxin-producing *C. perfringens* type A. Although the clinical illness is usually very short, mortality in an unprotected poultry flock can be devastating. Often the only sign of necrotic enteritis in a flock is a sudden increase in mortality. In addition to increased mortality, necrotic enteritis may present as birds with depression, ruffled feathers, and dark diarrhea. The disease persists in a flock for between about 5-10 days, with mortality between 2-50%. Necrotic enteritis can be controlled by antimicrobial drugs administered at prophylactic doses either in water or in feed; however, there is increasing public opposition to the use of antibiotics in animal feeds.

In the European Union (EU) antimicrobial growth promotants (AGPs) were banned from animal feeds on Jan. 1, 2006 (Regulation 1831/2003/EC) because of concerns about the increasing prevalence of antibiotic resistances among bacteria (Huyghebaert et al. 2011. *Vet. J.* 187:182-188; Millet and Maertens. 2011. *Vet. J.* 187:143-144). In 2015, the state of California passed a law banning the routine use of antibiotics in livestock (Retrieved from the Internet: mercurynews.com/california/ci_28951303/antibiotics). Earlier in 2015, McDonald's, the fast-food corporation, announced that it was going to use antibiotic-free chickens (Retrieved from the Internet:nytimes.com/2015/03/05/business). These events are likely precursors to further bans of the use of antibiotics in animal-feed in other states, or even a national ban in the U.S., within the next few years. Without traditional antibiotics for the prevention of necrotic enteritis and other diseases caused by *C. perfringens*, such diseases could potentially become a far greater problem for the livestock industry. Removal of these antimicrobials will dictate the need for alternative antimicrobials in order to achieve the same high level of food-animal production achieved with AGPs. Also changes within the gastrointestinal microbial flora of food-producing animals will result in the need for a more complete understanding of the gut microbial ecology (Wise & Siragusa. 2007. *J Appl. Microbiol.* 102:1138-1149; Oakley et al. 2013. *Plos One* 8(2): e57190) so that appropriate antibiotic alternatives may be developed for use during food-animal production (Seal et al. 2013. *Anion. Health Res. Rev.* 14:78-87).

Prior to the discovery and widespread use of antibiotics, bacterial infections were treated by administering bacteriophages and were marketed by L'Oreal in France. Although Eli Lilly Co. marketed phage products for human use until the 1940's, early clinical studies with bacteriophages were not extensively undertaken in the United States and Western Europe after that time. Bacteriophages were and continue to be sold in the Russian Federation and Eastern Europe as treatments for bacterial infections (Sulakvelidze et al. 2005. *Drug Discovery Today* 10:807-809). There has been a resurgent interest in bacteriophage biology and use of phage gene products as antibacterial agents (Liu et al. 2004. *Nature Biotech.* 22:185-191; Pastagia et al. 2013. *J. Med. Microbiol.* 62:1506-1516; Schmelcher et al. 2012. *Future Microbiol.* 7:1147-1171; Rodriguez-Rubio et al. 2014. *Crit. Rev. Microbiol.* 39:427-434; Seal, B. S. 2013. *Poultry Sci.* 92:526-533). The potential use of lytic bacteriophages and/or their lytic enzymes has been of considerable interest for veterinary and human medicine, as well as the bioindustry worldwide due to antibiotic resistance issues among bacterial pathogens. Recently, the U.S. Food and Drug Administration approved a mixture of anti-*Listeria* viruses as a food additive to be used in processing plants for spraying onto ready-to-eat meat and poultry products to protect consumers from *Listeria monocytogenes* (Bren, L. 2007. *FDA Consum.* 41:20-22). Although bacteriophages have been considered as potentially important alternatives to antibiotics (Sulakvelidze et al., supra; Lu and Koeris. 2011. *Curr. Opin. Microbiol.* 14:524-531; Maura and Debarbieux. 2011. *Appl. Microbiol. Biotech.* 90:851-859), it is important to emphasize that development of bacterial resistances to their viruses occurs. Evolution of phage receptors, super-infection exclusion, restriction enzyme-modification systems and abortive infection systems such as bacterial CRISPR sequences are all mechanisms that bacteriophage hosts utilize to avoid infection (Labrie et al. 2010. *Nature Rev. Microbiol.* 8:317-327), arguing for use of bacteriophage lytic proteins.

Antibiotic resistance among pathogens is believed to develop, in part, through the use of broad range antibiotics, which affect not only the target pathogen, but can also select for resistance in other bacteria (e.g. commensals). The use of a highly specific antimicrobial would target fewer species, and thus is less likely to contribute to the broad range resistance development now apparent with commonly used broad range antibiotics. Bacteriophage endolysins are uniquely specific to their host (or closely related species); bacteriophage and bacterial hosts have co-evolved. It is difficult to prove that resistance cannot develop to endolysins, but to date, none has been reported and this fact alone makes this product a candidate for addition to the battery of antimicrobials available to both veterinary medicine and the clinician. If resistant strains are not produced, this would be an important antimicrobial for use and efficacy.

SUMMARY OF THE INVENTION

Without traditional antibiotics for the prevention of animal diseases caused by *C. perfringens*, such diseases could potentially become a far greater problem. Removal of antibiotics will dictate the need for alternative antimicrobials in order to achieve the same high level of food-animal production achieved with AGPs. Thus, to manage the upsurge of drug resistant pathogenic bacteria, there is a need for new specific antimicrobial treatments. Reagents developed specifically for the relevant genera, species or substrains of concern would function as effective tools for controlling economically important diseases and therefore are ideal candidates for therapeutic treatments.

We have discovered nucleic acid molecules encoding the peptidoglycan hydrolases: PlyCP10, PlyCP18, PlyCP33, and PlyCP41. PlyCP18 and PlyCP33 harbor L-alanine amidase catalytic domains, and PlyCP10 and PlyCP41 have glycosyl hydrolase catalytic domains which specifically attack the peptidoglycan cell wall of *Clostridium perfringens*.

In accordance with this discovery, it is an object of the invention to provide nucleic acid molecules encoding the antimicrobial PlyCP10, PlyCP18, PlyCP33, and PlyCP41 lytic proteins.

It is a further object of the invention to provide cDNAs encoding antimicrobial proteins which are capable of specifically lysing as many as 66 *C. perfringens* strains (including chicken and porcine isolates) but not the other bacteria tested.

An additional object of the invention is to provide a host organism into which the plyCP10, plyCP18, plyCP33 and plyCP41 cDNAs, according to the invention can be introduced so as to produce an endolysin or truncated endolysin.

A further object of the invention is to provide a composition(s) useful for the treatment of disease caused by *C. perfringens* for which the PlyCP10, PlyCP18, PlyCP33, and PlyCP41 endolysins are specific and effective, wherein said composition comprises PlyCP10, PlyCP18, PlyCP33, and/or PlyCP41 and a pharmaceutically acceptable carrier.

An additional object of the invention is to provide compositions useful for the treatment of disease comprising the composition above in combination with another compositions having one or more disease-resistance properties.

Another object of the invention is to provide a composition in the form of a nutritional supplement or a feed supplement containing the composition comprising PlyCP10, PlyCP18, PlyCP33, and/or PlyCP41 wherein said nutritional supplement or feed supplement is particularly for feeding livestock including poultry and other animals.

Also part of this invention is a kit, comprising a composition for treatment of disease caused by the bacteria for which the PlyCP10, PlyCP18, PlyCP33, and PlyCP41 endolysins are specific. Other objects and advantages of this invention will become readily apparent from the ensuing description.

BRIEF DESCRIPTION OF THE DRAWINGS

FIG. 1A is a schematic representations of endolysin PlyCP10. FIG. 1B depicts both SDS-PAGE and zymogram gel analyses. Lanes 1 and 3: markers; Lane 2: 15% SDS-PAGE gel; and Lane 4: Zymogram with CP39 cells embedded into gel. FIG. 1C depicts the Spot Lysis Assay. Ten µl of protein were spotted onto CP39 cells in top agar.

FIG. 2A is a schematic representations of endolysin PlyCP18; PlyCP18 is 309 amino acids in length. The N-terminal 6×His tag and start codon add 7 amino acids. FIG. 2B depicts both SDS-PAGE and zymogram gel analyses. Lanes 1 and 3: markers; Lane 2: 15% SDS-PAGE gel; and Lane 4: Zymogram with CP39 cells embedded into gel. FIG. 2C depicts the Spot Lysis Assay. Ten µl of protein were spotted onto CP39 cells in top agar.

FIG. 3A is a schematic representations of endolysin PlyCP33. FIG. 3B depicts both SDS-PAGE and zymogram gel analyses. Lanes 1 and 3: markers; Lane 2: 15% SDS-PAGE gel; and Lane 4: Zymogram with CP39 cells embedded into gel. FIG. 3C depicts the Spot Lysis Assay. Ten µl of protein were spotted onto CP39 cells in top agar.

FIG. 4A is a schematic representations of endolysin PlyCP41. FIG. 4B depicts both SDS-PAGE and zymogram gel analyses. Lanes 1 and 3: markers; Lane 2: 15% SDS-PAGE gel; and Lane 4: Zymogram with CP39 cells embedded into gel. FIG. 4C depicts the Spot Lysis Assay. Ten µl of protein were spotted onto CP39 cells in top agar.

DETAILED DESCRIPTION OF THE INVENTION

Figure 1A:
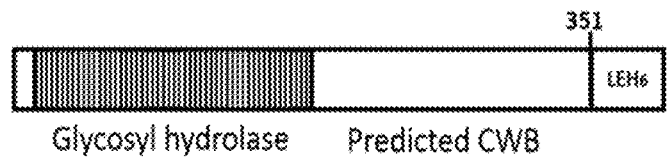
FIGS. 1A, 1B and 1C describe characteristics of *C. perfringens* phage endolysin PlyCP10.

What is needed in the art are alternatives to traditional antibiotics which are effective in preventing and treating disease caused by *C. perfringens*, especially *C. perfringens* that affect poultry and are highly refractory to resistance development. Bacterio-lytic proteins like endolysins have great potential for controlling bacteria. Bacteriophage are viruses that infect bacteria. Some bacteriophage integrate their genome into the genome of their bacteria host and become dormant prophages. Endolysins are encoded in bacteriophage (and prophage) genomes, and are used by the bacteriophage to lyse their host cells, in order to cause the release of replicated bacteriophage particles. Endolysins cause this lysis by degrading the peptidoglycan of the cell wall of the bacteria, resulting in cells bursting open; cell lysis. The site of action is external to the pathogen, and thus avoids many of the intracellular drug resistance mechanisms e.g. efflux pumps. Also, the phage and host have co-evolved, allowing the phage endolysin to have evolved to target sites in the cell wall that are difficult for the bacterium to mutate. Thus, it is believed that phage endolysins are highly refractory to resistance development. This characteristic makes endolysins a good source of anti-bacterial agents against Gram-positive bacteria, like *C. perfringens*.

Bacterial peptidoglycan has a complex structure (sugar backbone of alternating units of N-acetyl glucosamine (GlcNac) and N-acetyl muramic acid (MurNac) residues, cross-linked by oligopeptide attachments at the MurNac). Endolysins have evolved a modular design to deal with this complexity. One protein can harbor multiple domains, each with a different peptidoglycan digestion activity. Three classes of endolysin domains have been identified thus far: endopeptidase, glycosidase, and amidase. Each has been localized to short protein domains (~100-200 amino acids). Any one of these domains is sufficient to lyse the bacterial target cell.

Host strain specificity that has routinely been observed relative to the bacteriophages isolated from various *C. perfringens* isolates is probably due to evolution of the receptor and anti-receptor molecules. Consequently, several new antimicrobial agents, putative endolysins encoded by the genomes of clostridial bacteriophages, have been identified in our laboratories for use as potential antimicrobials to control *C. perfringens* (Seal et al. 2013, supra and references therein). In this study, we identify, express, and characterized four new endolysins derived from *C. perfringens* prophage sequences and identified the antimicrobial activities of PlyCP10, PlyCP18, PlyCP33, and PlyCP41.

Phage endolysins are known to be modular in structure (Diaz et al. 1990. *Proc. Natl. Acad. Sci. U.S.A.* 87:8125-8129; Donovan et al. 2006a. *Appl. Environ. Microbiol.* 72:2988-2996; Garcia et al. 1990. Gene 86:81-88), and there are numerous examples where single domains are functional without the need for the second lytic domain or the cell wall binding domain (Becker et al. 2009. *FEMS Microbiol. Lett.* 294:52-60; Donovan et al. 2006b. *Appl. Environ. Microbiol.* 72:5108-5112; Donovan et al. 2006c. *FEMS Microbiol. Lett.* 265:133-139).

The His-tagged recombinant phage endolysin-derived proteins PlyCP10, PlyCP18 (C-terminal His tag), PlyCP18 (N-terminal His tag), PlyCP33, and PlyCP41 are identified by SEQ ID NO: 2, SEQ ID NO: 4, SEQ ID NO: 6, SEQ ID NO: 8 and SEQ ID NO: 10, respectively. The nucleic acid sequences encoding these proteins, i.e., SEQ ID NO: 1, SEQ ID NO: 3, SEQ ID NO: 5, SEQ ID NO: 7 and SEQ ID NO: 9, respectively, include the engineered nucleotides encoding the 2 amino acid residues encoded by the restriction enzyme cloning site and the six histidine tag required for nickel chromatography purification. The encoding sequences of the individual modules of the phage PlyCP10, PlyCP18, PlyCP33, and PlyCP41 endolysins according to the invention can be assembled by any usual method for constructing and assembling nucleic acid fragments which are well known to those skilled in the art and widely described in the literature and illustrated especially by the use examples of the invention. There are two versions of PlyCP18; both C- and N-terminal 6×His tagged proteins were produced (SEQ ID NO: 4 and 6, respectively). There was <2× difference in specific activity between the proteins isolated from these two versions in the turbidity reduction assay, so they have been used interchangeably in the data presented.

Antimicrobial activity was characterized with two quantitative peptidoglycan hydrolase assays, the turbidity reduction assay and the plate lysis assay, as described previously (Donovan and Foster-Frey, supra).

The present invention also relates to a chimeric gene (or expression cassette) comprising an encoding sequence as well as heterologous regulatory elements in positions 5' and 3' which can function in a host organism, the encoding sequence comprising at least one nucleic acid sequence encoding a phage PlyCP10, PlyCP18, PlyCP33, and PlyCP41 endolysin related protein (truncation or fusion) as defined above. By host organism there is to be understood any single-celled or lower or higher non-human multi-celled organism into which a phage endolysin gene according to the invention can be introduced. The regulatory elements required for expressing the nucleic acid sequence encoding a phage endolysin are well known to those skilled in the art and depend on the host organism. The means and methods for identifying and choosing the regulatory elements are well known to those skilled in the art and widely described in the literature.

The present invention also relates to a cloning and/or expression vector for transforming a host organism containing at least one of the phage endolysin genes as defined hereinabove (plyCP10, plyCP18, plyCP33, and plyCP41). This vector comprises, in addition, to the above phage plyCP10, plyCP18, plyCP33, and plyCP41 endolysin genes, at least one replication origin. This vector can be constituted by a plasmid, a cosmid, a bacteriophage or a virus which is transformed by introducing the chimeric gene according to the invention. Such transformation vectors according to the host organism to be transformed are well known to those skilled in the art and widely described in the literature.

A further subject of the invention is a process for the transformation of host organisms, by integrating a least one nucleic acid sequence or chimeric gene as defined hereinabove, which transformation may be carried out by any suitable known means which have been widely described in the specialist literature and in particular in the references cited in the present application, more particularly by the vector according to the invention.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the phage PlyCP10, PlyCP18, PlyCP33, and PlyCP41 endolysins according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "transgene" is understood to describe genetic material which has been or is about to be artificially inserted into the genome of a non-human animal or microbe, and particularly into a cell of a living non-human mammal. It is to be understood that as used herein the term "transgenic" includes any microbe, cell, cell line, or tissue, the genotype of which has been altered by the presence of a heterologous nucleic acid including those transgenics initially so altered as well as those created by sexual crosses or asexual propagation from the initial transgenic.

The term "transformation" refers to a permanent or transient genetic change induced in a cell following the incorporation of new DNA (i.e. DNA exogenous to the cell).

Where the cell is a microbe or mammalian cell, a permanent genetic change is generally achieved by introduction of the DNA into the genome of the cell. When the cell is a bacterial or microbial cell, the term can refer to an extrachromosomal, self-replicating vector which harbors a selectable antibiotic resistance or genome integrated form. Thus, isolated polynucleotides of the present invention can be incorporated into recombinant constructs, typically DNA constructs, capable of introduction into and replication in a host cell, whether that cell be a eukaryote, archaea, or bacteria. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence (s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes the functional phage PlyCP10, PlyCP18, PlyCP33, and PlyCP41 endolysin polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of phage PlyCP10, PlyCP18, PlyCP33, and PlyCP41 endolysins" refers to all fragments of phage PlyCP10, PlyCP18, PlyCP33, and PlyCP41 endolysins that retain phage PlyCP10, PlyCP18, PlyCP33, and PlyCP41 endolysin activity and function to lyse C. perfringens bacteria.

Modifications of the phage PlyCP10, PlyCP18, PlyCP33, and PlyCP41 endolysin primary amino acid sequences may result in further mutant or variant proteins having substantially equivalent activity to the phage PlyCP10, PlyCP18, PlyCP33, and PlyCP41 endolysin polypeptides described herein. Such modifications may be deliberate, as by site-directed mutagenesis, or may occur by spontaneous changes in amino acid sequences where these changes produce modified polypeptides having substantially equivalent activity to the phage PlyCP10, PlyCP18, PlyCP33, and PlyCP41 endolysin polypeptides. Any polypeptides produced by minor modifications of the phage PlyCP10, PlyCP18, PlyCP33, and PlyCP41 endolysin primary amino acid sequence are included herein as long as the biological activity of phage PlyCP10, PlyCP18, PlyCP33, and PlyCP41 endolysin is present; e.g., having a role in pathways leading to lysis of staphylococcal bacteria. For example, two versions of PlyCP18; both C- and N-terminal 6×His tagged proteins were produced (SEQ ID NO: 4 and 6, respectively). There was <2× difference in specific activity between the two protein isolates in the turbidity reduction assay, so they have been used interchangeably in the data presented. The His-tagged recombinant phage endolysin-derived proteins PlyCP10, PlyCP18 (C-terminal His tag), PlyCP18 (N-terminal His tag), PlyCP33, and PlyCP41 are identified by SEQ ID NO: 2, SEQ ID NO: 4, SEQ ID NO: 6, SEQ ID NO: 8 and SEQ ID NO: 10, respectively. The nucleic acid sequences encoding these proteins, i.e., SEQ ID NO: 1, SEQ ID NO: 3, SEQ ID NO: 5, SEQ ID NO: 7 and SEQ ID NO: 9, respectively.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

Thus, isolated sequences that encode any one of the phage PlyCP10, PlyCP18, PlyCP33, and PlyCP41 endolysin polypeptides and which hybridize under stringent conditions to the phage PlyCP10, PlyCP18, PlyCP33, and PlyCP41 endolysin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid sequences and nucleotide sequences encoding polypeptides that comprise particular phage proteins. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have phage PlyCP10, PlyCP18, PlyCP33, and PlyCP41 endolysin-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the phage PlyCP10, PlyCP18, PlyCP33, and PlyCP41 endolysin polypeptides of the invention. Naturally occurring allelic variants such as these can be identified with the use of well-known molecular biology techniques, as, for example, with polymerase chain reaction (PCR), a technique used for the amplification of specific DNA segments, and DNA sequencing. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, phage PlyCP10, PlyCP18, PlyCP33, and PlyCP41 endolysin activity as described herein. Such variants may result from, for example, genetic polymorphism or from human manipulation. Biologically active variants of a native phage PlyCP10, PlyCP18, PlyCP33, and PlyCP41 endolysin proteins of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired phage PlyCP10, PlyCP18, PlyCP33, and PlyCP41 endolysin activity.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of phage PlyCP10, PlyCP18, PlyCP33, and PlyCP41 endolysin protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The *C. perfringens* control compositions of the invention comprise the antimicrobial composition of the invention dissolved or suspended in an aqueous carrier or medium.

The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The compositions of this invention comprise ingredients which are generally regarded as safe, and are not of themselves or in admixture, incompatible with human and veterinary applications.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

An oral composition can generally include an inert diluent or an edible carrier. The nutraceutical composition can comprise a functional food component or a nutrient component. The term "functional food" refers to a food which contains one or a combination of components which affects functions in the body so as to have positive cellular or physiological effects. The term "nutrient" refers to any substance that furnishes nourishment to an animal.

The preferred compositions of this invention comprise ingredients which are nutritional supplements or feed supplements used for feeding livestock, in particular, poultry. The terms feed supplement, nutritional supplement or feed additive are used herein interchangeably unless otherwise indicated. The terms are to be understood as an ingredient or a mixture or combination of ingredients which can be mixed to a feed to fulfill one or more specific need(s), for example, as part of a diet. The feed additive may be a component of a feed product. The feed product containing the feed additive according to the present invention may contain further suitable other components like cereal products, protein raw material, fiber raw material and lignocelluloses-containing raw material. Moreover, the feed product may contain at least one of the components selected from trace elements, vitamins, tallow, enzymes, minerals and common additives added to feed products especially for poultry. Further, the term "feed" here is not restricted exclusively to substances which would normally be described as feed, but also refers to nutritional additives, e.g. yeast, starch, various types of sugar, etc.

Likewise, ingredients may be selected for any given composition which are cooperative in their combined effects whether incorporated for antimicrobial efficacy, physical integrity of the formulation or to facilitate healing and health in medical and veterinary applications. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Bacterial Cultures, Propagation of Strains

All strains used in this work are listed in Table 1. Poultry *C. perfringens* strains Cp6 to Cp1038 were a gift from Bruce Seal (Poultry Microbiology Safety Research Unit, Agricultural Research Service, U.S. Department of Agriculture, Athens, Ga., USA), porcine *C. perfringens* strains JGS 1073, JGS 1090, JGS 1504, JGS 1508, JGS 1544, JGS 1564, JGS 1659, JGS 1756, and JGS 1905 were a gift from Nancy Cornick (Veterinary Microbiology and Preventive Medicine, Iowa State University, Ames, Iowa, USA), bovine *C. perfringens* strains M17-17498, M17-19288, M17-20950, M17-22227, M17-22698, WVDL-17, WVDL-23, and WVDL-24 were a gift from Nicole Aulik and Donald Sockett (Wisconsin Veterinary Diagnostic Laboratory), and strains ATCC-12916 and ATCC-13124 were from the American Type Culture Collection (Manassas, Va., USA). *Enterococcus faecalis* strain EF-17 was a gift from Paul Hyman (Biology & Toxicology Department, Ashland University, Ashland, Ohio, USA). *E. coli* DH5α was from Invitrogen™. The *Streptococcus uberis, Streptococcus agalactiae*, and *Staphylococcus aureus* strains were a gift from Max J. Paape (USDA, Beltsville, Md., USA) *C. perfringens* strains were cultivated anaerobically at 37° C. in BYC media (37 g/L Brain Heart Infusion, 5 g/L yeast extract, 0.5 g/L L-cysteine free base) without shaking. *C. perfringens* colonies were produced from streakouts on BYC agar plates (BYC+15 g agar per liter) incubated in an anaerobic jar with AnaeroGen™ satchets (Oxoid, Hampshire, England) at 37° C. All other bacteria, tested for lysis by endolysins, were cultured aerobically at 37° C. in tryptic soy broth or brain heart infusion media.

The *C. perfringens* genome sequences were examined for genes encoding L-alanine amidase or glycosyl hydrolase domains near predicted phage genes. The genes for PlyCP10, PlyCP18, PlyCP33 and PlyCP41 were found within prophage regions of the genomes of their corresponding strains CP10, Cp18, CP33 and CP41 (Siragusa et al. 2006. *J. Clin. Microbiol.* 44:1065-1073) using search tools at the Integrated Microbial Genomes (IMG) website (Retrieved from the internet: img.jgi.doc.gov/). The four genes were each found adjacent to predicted holin genes and other phage related sequences, and therefore are predicted to be phage endolysins. These genes were *E. coli* codon-optimized, synthesized, and cloned into *E. coli* expression vectors using NdeI and XbaI restriction sites, by GenScript™ to yield PlyCP10-pET21a, PlyCP18-pET21a, PlyCP33-pET21a and PlyCP41-pET21a. The resulting proteins encoded in the plasmid have the following amino acids added at the C-terminus, LEHHHHHH, from the adjacent plasmid sequences. Additionally, PlyCP18 was PCR-amplified with primers that engineered an NdeI site and 6×His tag at the N-terminal, and both a stop codon and BamHI site at the C-terminus. This amplicon was cloned into pET11a using NdeI and BamHI restriction enzymes, to make PlyCP18-pETNH, which adds amino acids MHHHHHHS to the N-terminus of PlyCP18, and removes the LEHHHHHH from the C-terminus. These plasmids were used to transform BL21 (DE3) *E. coli* (Invitrogen™) by the manufacturer's protocols. Schematics of the recombinant proteins are presented in FIGS. 1A, 2A, 3A and 4A.

The plyCP10 gene was identified in the genome of strain Cp10 (Siragusa et al., supra). PlyCP10 has an N-terminal glycosyl hydrolase family 25 catalytic domain by PFAM search (FIG. 1A). The C-terminal half of PlyCP10 does not have significant functional domain homology by PFAM or BLASTP analysis but does show weak (insignificant) homology to the SH3b cell wall binding domain by the HMMER analysis offered by EMBL-EBI. Its nearest neighbors from BLASTP analysis are Genbank protein WP_003469445 with 99% coverage at 84% identity, and Genbank protein WP_011010411 with 82% coverage at 87% identity; both predicted glycosyl hydrolases.

Figure 2A:
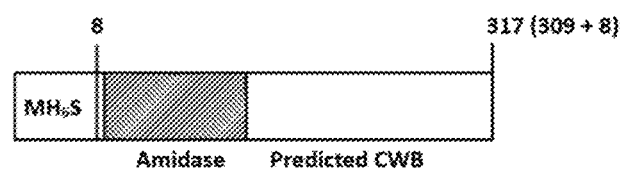
FIGS. 2A, 2B and 2C describe characteristics of *C. perfringens* phage endolysin PlyCP18.

The second lysin gene, plyCP18, was found in the genome of strain Cp18 (Siragusa et al., supra). PlyCP18 has an N-terminal L-alanine amidase, family 2, catalytic domain by PFAM search (FIG. 2A). The C-terminal half of PlyCP18 does not have significant functional domain homology by PFAM or BLASTP analysis but does show weak (insignificant) homology to the SH3b cell wall binding domain by the HMMER analysis offered by EMBL-EBI. Its nearest neighbors from BLASTP analysis are Genbank protein WP_060796135 with 52% coverage at 86% identity, and Genbank protein WP_011010276 with 62% coverage at 70% identity; both predicted L-alanine amidases. The third highest scoring BLASTP hit was Genbank protein WP_003469445, which was the first hit for PlyCP10. PlyCP10 and PlyCP18 share high homology over the C-terminal half of the protein suggesting a common cell wall binding domain type; currently not defined by PFAM. There are two versions of PlyCP18; both C- and N-terminal 6xHis tagged proteins were produced (SEQ ID NO: 4 and 6, respectively). There was <2x difference in specific activity between the two in the turbidity reduction assay, so they have been used interchangeably in the data presented.

Figure 3A:
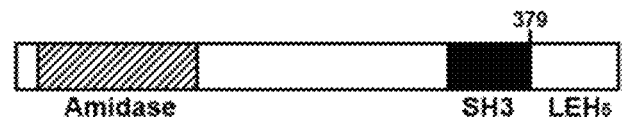
FIGS. 3A, 3B and 3C describe characteristics of *C. perfringens* phage endolysin PlyCP33.

The third lysin gene, plyCP33, was found in the genome of strain Cp33 (Siragusa et al., supra). PlyCP33 has an N-terminal L-alanine amidase, family 2, catalytic domain by PFAM search (FIG. 3A). The C-terminus of PlyCP33 has a SH3 domain by PFAM and BLASTP analysis with predicted cell wall binding function. The middle section of the protein does not have a functional domain by PFAM or BLASTP analysis, but likely harbors another cell wall binding or catalytic domain of unfamiliar composition. BLASTP found three L-alanine amidases, with strong homology to PlyCP33: WP_061427607 with 100% coverage at 93% identity, with 100% coverage at 91% identity, and YP_008058948 with 99% coverage at 74% identity. YP_008058948, encoded by the phiCP51L gene, is the previously characterized endolysin, CP25L (Gervasi et al. 2014. *Appl. Microbiol. Biotechnol.* 98:2495-2505).

The fourth lysin gene, plyCP41, was found in the genome of strain Cp41 (Siragusa et al., supra). PlyCP41 has an N-terminal glycosyl hydrolase family 25 domain, and the C-terminal half has two SH3 domains common to cell wall binding domains by PFAM analysis. BLASTP analysis yielded several hits with 100% coverage and 97% to 92% identity: WP_004461179, WP_003469359, WP_003465496, and WP_057231813.

Example 2

Protein Expression, Purification and SDS-PAGE Analysis

The recombinant endolysin proteins were expressed and purified essentially as described previously (Abaev et al. 2013. *Appl. Microbiol. Biotechnol.* 97(8):3449-3456). Briefly, BL21 (DE3) *E. coli* (Invitrogen™) carrying endolysin expression plasmids, pET variants, were propagated in 1 L Luria Bertani (LB) broth supplemented with 150 µg/mL ampicillin at 37° C. (shaking at 225 rpm) until the $OD_{600}$ reading was 0.4-0.6 (log phase growth). The broth culture was held on ice for 15 minutes and then treated with 1 mM isopropyl-β-D-1-thiogalactopyranoside (IPTG) for induction of the peptidoglycan hydrolase gene. The induced cells were then incubated with shaking 18 hours at 10° C. The culture was centrifuged for 30 min at 6000 rpm. The supernatant was removed, the pellet was suspended in protein purification buffer (50 mM $NaH_2PO_4$, 300 mM NaCl, 10 mM imidazole, 30% glycerol, pH 8.0) and the suspended cells were lysed by sonication. The lysate was centrifuged for 30 min at 7500 rpm to pellet the cell debris. The resultant supernatant was purified via Nickel-NTA column chromatography following manufacturer's instructions (Qiagen™). The purified recombinant endolysin in elution buffer (50 mM $NaH_2PO_4$ 250 mM imidazole 300 mM NaCl 30% glycerol pH 8.0) and the cellular lysate were analyzed by 15% acrylamide SDS-PAGE and stained with Coomassie Blue to confirm the purity of the expressed protein (1990. *Gel Electrophoresis of Proteins: A Practical Approach*, Hames, B. D. and Rickwood, D., Eds., Oxford University press, New York, N.Y., pages 1-147). Zymogram gels were made the same as the SDS-PAGE gels but incorporated ~300 mL culture equivalent (after centrifugation harvesting) of mid-log phase CP39 cells in the gel (Abaev et al., supra). Zymogram gels were run, then incubated in $H_2O$ to remove the SDS, and then incubated at room temperature in PBS 1% Triton X-100 pH8 for enzyme refolding and lytic activity for 2 to 24 hours before photodocumenting the results.

Figure 1B:
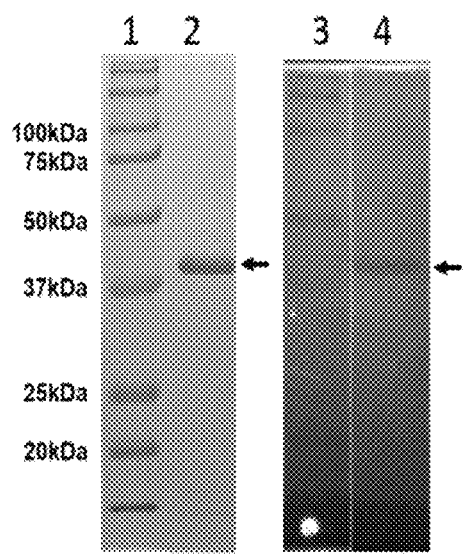
Figure 1C:
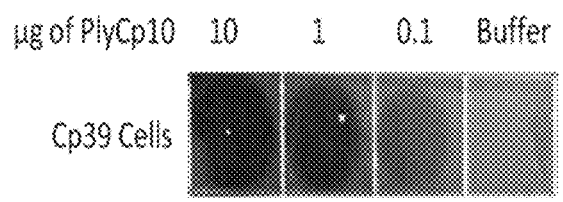

The recombinant PlyCP10 protein with a C-terminal 6xHis tag (FIG. 1A) was expressed, purified by nickel chromatography, and characterized via SDSPAGE and zymogram analysis. The recombinant PlyCP10 appears as a ~40 kDa band by SDSPAGE (FIG. 1B), which is in agreement with the predicted size of 41058 Da for the recombinant protein. The zymogram gel also shows a single band at ~40 kDA (FIG. 1B), indicating that only this band is necessary for lytic activity.

The recombinant PlyCP18 protein with an N-terminal 6xHis tag (FIG. 2A) was expressed, purified by nickel chromatography, and run on SDSPAGE and zymogram gels. The recombinant PlyCP18 appears as a ~36 kDa band by SDSPAGE (FIG. 2B), which is in agreement with the predicted size of 36677 Da for the recombinant protein. The zymogram gel also shows a single band at ~36 kDA (FIG. 2B), indicating that only this band is necessary for lytic activity. This protein, PlyCP18, is 309 amino acids long, with a predicted molecular weight of 35635. In recombinant form, with the amino acids LEHHHHHH added to the C-terminus of the protein, the predicted molecular weight is 36700.

Figure 2B:
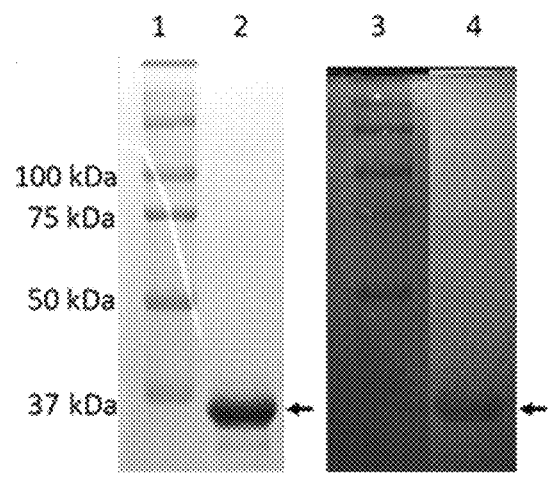
Figure 2C:
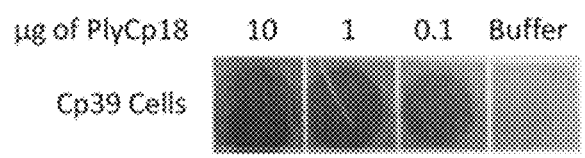
Figure 3B:
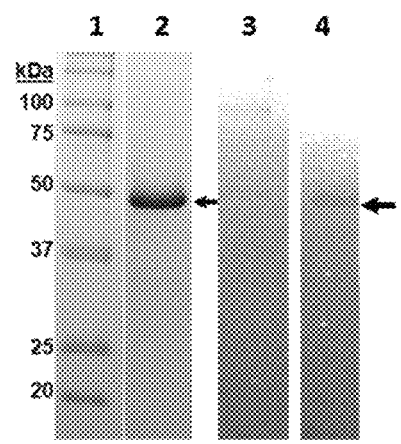
Figure 3C:
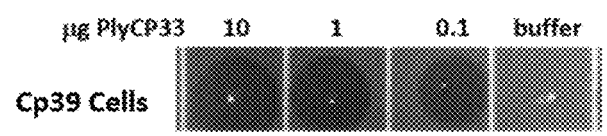

The recombinant PlyCP33 protein with a C-terminal 6xHis tag was expressed, purified by nickel chromatography, and run on SDSPAGE and zymogram gels. PlyCP33 appears as a ~48 kDa band by SDSPAGE (FIG. 3B), which is slightly larger, though not unusually so, than the predicted size of 44621 Da for the recombinant protein. The zymogram gel also shows a single band at ~48 kDA (FIG. 3B), indicating that only this band is necessary for lytic activity. The endolysin PlyCP33 is an amidase belonging to a subgroup or family defined by PFAM as amidase_2. This protein also has a predicted SH3 domain, which is associated with cell wall binding. The middle section has no defined domain, but likely contains another binding or catalytic activity. This protein, PlyCP33, is 379 amino acids long, with a predicted molecular weight of 43555. In recombinant form, with the amino acids LEHHHHHH added to the C-terminus of the protein, the predicted molecular weight is 44620. The purified protein migrates just below the 50 kDa marker, which is in agreement with its predicted size (FIG. 2B, lane 2).

Figure 4A:
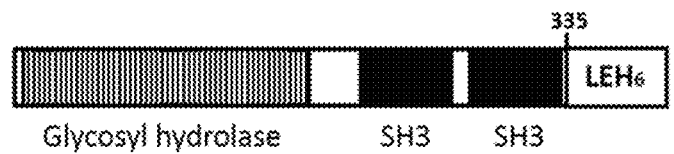
FIGS. 4A, 4B and 4C describe characteristics of *C. perfringens* phage endolysin PlyCP41.
Figure 4B:
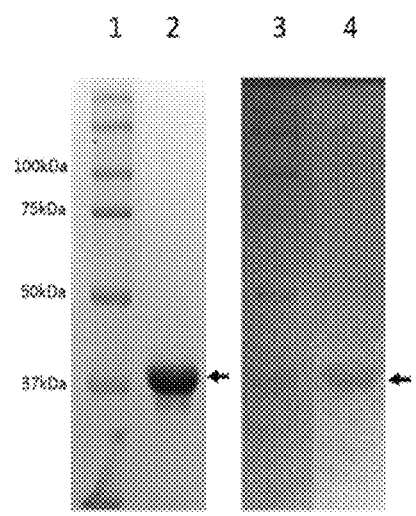
Figure 4C:
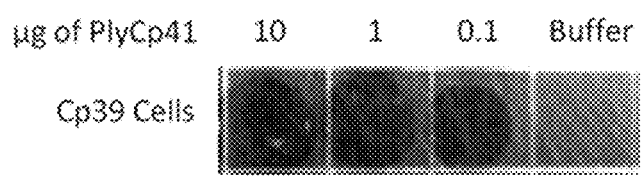

The recombinant PlyCP41protein with a C-terminal 6×His tag (FIG. 4A) was expressed, purified by nickel chromatography, and run on SDSPAGE and zymogram gels. The recombinant PlyCP41 appears as a ~39 kDa band by SDSPAGE (FIG. 4B), which is in agreement with the predicted size of 39600 Da for the recombinant protein. The zymogram gel also shows a single band at ~39 kDA (FIG. 4B), indicating that only this band is necessary for lytic activity. The endolysin PlyCP41 is a glyosidase belonging to a subgroup or family defined by PFAM as glycosyl hydrolase 25, or GH25 (FIG. 3A). In the C-terminal half, there are SH3 domains, which are usually associated with cell wall binding domains. This protein, PlyCP41, is 335 amino acids long, with a predicted molecular weight of 38637. In recombinant form, with the amino acids LEHHHHHH added to the C terminus of the protein, the predicted molecular weight is 39702. The purified protein migrates just above the 37 kDa marker, which is in agreement with its predicted size (FIG. 4B, lane 2). It also displayed activity against *C. perfringens* cells embedded in a zymogram gel (FIG. 4B, lane 4).

Example 3

Spot Lysis Assay

The plate lysis (spot on lawn) assay was essentially as described previously (Becker et al., supra). *C. perfringens* cultures were propagated to mid-log phase ($OD_{600}$=0.4-0.6) in 100 mL BYC media. Cells were harvested via centrifugation at 5,000 g for 30 min., resuspended in 2 mL PBS 25% glycerol and stored at −80° C. until needed. The frozen cell pellet was thawed on ice, and washed with 10 mL sterile $H_2O$. The cells were then washed once with 0.5× lysin buffer A and then a final time with 10 mL 1× lysin buffer A (50 mM $NH_4OAc$, 10 mM $CaCl_2$, 1 mM DTT, pH 6.2) and pelleted again. The cells were suspended in 1.0 mL lysin buffer A. Twelve milliliters of melted 50° C. semisolid BYC agar (BYC media with 7 g agar per liter, autoclaved 20 min) were added to the cells and then the mixture was poured into a sterile square petri dish. This was allowed to sit 20 min at room temperature to solidify and then 10 μl of the Ni-chromatography purified endolysin was spotted onto the plate and allowed to air dry 20 min. The plate was incubated in an anaerobic chamber for 2 hours at 37° C. before scoring for clear zones. A handful of strains were not amenable to the conditions of the spot lysis assay, and were instead tested by turbidity reduction assay.

Spot lysis assay of 10, 1, 0.1 μg of purified PlyCP10 enzyme shows that 0.1 μg is sufficient to lyse strain Cp39 (FIG. 1C). PlyCP10, at the lowest concentration tested, was capable of lysing all 66 strains of *C. perfringens* by spot lysis assay or by turbidity reduction and did not lyse the other species of bacteria tested (Table 1). Spot lysis assay of 10, 1, 0.1 μg of purified PlyCP18 enzyme shows that 0.1 μg is sufficient to lyse strain CP39 (FIG. 2C). PlyCP18 was capable of lysing all 66 strains of *C. perfringens* by spot lysis assay or by turbidity reduction (Table 1), and did not lyse the other species of bacteria tested. PlyCP18 had reduced activity against strain CP28 (Table 1).

Spot lysis assay of 10, 1, 0.1 μg of purified PlyCP33 enzyme shows that 0.1 μg is sufficient to lyse strain Cp39 (FIG. 3C). PlyCP33 was capable of lysing all 66 strains of *C. perfringens* by spot lysis assay or by turbidity reduction (Table 1), and did not lyse the other species of bacteria tested. PlyCP33 had reduced activity against strains Cp41 and Cp1113 (Table 1).

Spot lysis assay of 10, 1, 0.1 ug of purified PlyCP41enzyme shows that 0.1 μg is sufficient to lyse strain Cp39 (FIG. 4C). PlyCP41, at the lowest concentration tested, was capable of lysing all 66 strains of *C. perfringens* by spot lysis assay or by turbidity reduction and did not lyse the other species of bacteria tested (Table 1).

TABLE 1

Lytic activity of 4 endolysins against various isolates of *C. perfringens*.

| Bacterial Strain | CP Type | Endolysin PlyCP10 | PlyCP18 | PlyCP33 | PlyCP41 |
|---|---|---|---|---|---|
| *C. perfringens* (Pig isolates) | | | | | |
| JGS 1073, JGS 1090, JGS 1504, JGS 1564, JGS 1659, JGS 1756, JGS 1905 | C | +++ | +++ | +++ | +++ |
| JGS 1508* | C | +++ | +++ | ++ | +++ |
| JGS 1544* | C | ++ | +++ | ++ | +++ |
| *C. perfringens* (Meat isolates) | | | | | |
| ATCC 12916 | A | +++ | +++ | +++ | +++ |
| ATCC 13124 | A | +++ | +++ | +++ | +++ |
| *C. perfringens* (Chicken isolates) | | | | | |
| Cp6-Cp13, Cp15, Cp16, Cp18-Cp26, Cp29, Cp33-Cp35, Cp38, Cp39, Cp40, Cp42-Cp51, Cp53, Cp124, Cp136, Cp225, Cp503, Cp504, Cp509, Cp724, Cp725, Cp734, Cp741, Cp792, Cp854, | A | +++ | +++ | +++ | +++ |

TABLE 1-continued Lytic activity of 4 endolysins against various isolates of *C. perfringens*.

| Bacterial Strain | CP Type | Endolysin PlyCP10 | PlyCP18 | PlyCP33 | PlyCP41 |
|---|---|---|---|---|---|
| Cp1030, Cp1036, Cp1038 (51 Cp strains) | | | | | |
| Cp28 | A | +++ | + | +++ | + |
| Cp37* | A | +++ | +++ | ++ | ++ |
| Cp41* | A | +++ | ++ | + | ++ |
| Cp1113* | A | ++ | ++ | ++ | ++ |
| *C. perfringens* (Cow isolates) | | | | | |
| M17-17498, M17-19288, M17-22227, M17-22698, WVDL-23 | unknown | +++ | +++ | +++ | +++ |
| M17-20950, WVDL-17, WVDL-24 | unknown | ++ | +++ | +++ | +++ |
| Other Bacteria | | | | | |
| *E. faecelis* EF-17 | n.a. | − | − | − | − |
| *E. coli* DH5a | n.a. | − | − | − | − |
| *Streptococcus uberis* | n.a. | − | − | − | − |
| *Staphylococcus aureus* | n.a. | − | − | − | − |
| *Streptococcus agalactiae* | n.a. | − | − | − | − |

For the results shown in Table 1, ten μl of recombinant endolysin at 10 μg, 1 μg and 0.1 μg spotted onto cells embedded in top agar. Indication of results is as follows: "+++"=clearing was seen at all 3 concentrations; "++"=clearing was seen at two highest concentrations; "+"=clearing was only seen at highest concentration, "−"=no clearing was seen at any concentration. "*"=results based on data from Turbidity Reduction Assay, endolysins were considered active if activity was greater than that of the buffer control. Protein amounts were the same as in the spot lysis assay, but in a 0.2 mL assay volume. Lysostaphin and the phage λSA2 endolysin were used as positive controls for lysing some of the non-*Clostridium* bacteria. Some of the JGS strains are referenced in Sawires and Songer, supra.

All four endolysins were capable of lysing the 66 *C. perfringens* strains tested (including chicken and porcine isolates) but not the other species of bacteria tested.

Example 4

Turbidity Assay

The turbidity assay measures the drop in optical density (OD) resulting from lysis of the target bacteria with the phage endolysin-derived protein. If the lysin can digest the cell wall, lysis will occur with a subsequent reduction in OD. Changes in the $OD_{600nm}$ in the control sample (cells alone) were subtracted from samples containing both cells and lysin, before calculating the specific activity. Specific Activity=($\Delta OD_{600nm}$/min)/μM.

A modified turbidity reduction assay (Donovan et al., 2006) was completed using *C. perfringens* strain CP39 propagated anaerobically to mid-log phase ($OD_{600}$=0.4-0.6) in BYC media at 37° C. The cells were pelleted (3000 rpm, 15 min, 4° C.), washed three times and then suspended to an $OD_{600}$ of ~2 in sterile distilled water. In the wells of a 96 well plate, 0.1 mL cells were added to 0.1 mL endolysin (0.1, 1.0, or 10 μg) in lysin buffer A (50 mM NH4OAc 10 mM CaCl2 1 mM DTT pH6.8) and lytic activity was determined by a decrease in the absorbance $OD_{600}$ of the cell suspension in a SpectraMax 340 plate reader (Molecular Devices, Sunnyvale, Calif., USA) for 20 min at 22° C., taking readings every 20 s. Activity was calculated from the Vmax determined from the linear portion of each lysis curve using the Softmax Pro software (Molecular Devices, Sunnyvale, Calif., USA), subtracting out any decrease due to buffer alone, and data was normalized to the maximal activity from each experiment (Linden et al. 2015. *Appl. Microbiol. Biotechnol.* 99:741-752), or calculated for specific activity. Data points were obtained from triplicate data points. The turbidity reduction assay was used to measure the lytic activity of the endolysins PlyCP10, PlyCP18, PlyCP33, and PlyCP41 against *C. perfringens* JGS 1508, JGS 1544, Cp37, Cp41, and Cp1113.

Thus, the PlyCP10, PlyCP18, PlyCP33, and PlyCP41 endolysins are potent antimicrobials with uniquely active amidase and glycosyl hydrolase domains that will be good additions to future antimicrobial constructs. The PlyCP10, PlyCP18, PlyCP33, and PlyCP41 endolysin constructs can be used in novel environments to determine if the unique plate lysis phenotype is predictive of novel environments where this endolysin will find special application.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant cDNA which encodes an antimicrobial peptidoglycan hydrolase enzyme molecule, wherein said cDNA encodes an-amino acid sequence selected from the group consisting of SEQ ID NO: 2, SEQ ID NO: 4, SEQ ID NO: 6, SEQ ID NO: 8, and SEQ ID NO: 10.

2. The recombinant cDNA of claim 1, wherein said cDNA has a nucleic acid sequence selected from the group consisting of SEQ ID NO: 1, SEQ ID NO: 3, SEQ ID NO: 5, SEQ ID NO: 7, and SEQ ID NO: 9.

3. A construct comprising the recombinant cDNA of claim 1 operably linked to a heterologous promoter.

4. A vector comprising the construct of claim 3.

5. A host cell transformed with the cDNA according to claim 1.

6. A host cell transformed with the construct according to claim 3.

7. A method of making a recombinant peptidoglycan hydrolase protein, said method comprising:

introducing into a host cell a nucleic acid or construct encoding a peptidoglycan hydrolase protein having an amino acid sequence selected from the group consisting of SEQ ID NO: 2, SEQ ID NO: 4, SEQ ID NO: 6, SEQ ID NO: 8, and SEQ ID NO: 10;

culturing said cell under conditions suitable for expression of said protein; and recovering the protein so expressed.

8. The method of claim 7 wherein said host cell is a yeast cell and said peptidoglycan hydrolase protein is recovered as a purified protein; a partially purified yeast extract; or an unpurified protein within said yeast cell.

9. The method of claim 7 wherein said host cell is a bacterial cell, a fungal cell, a plant cell, or a mammalian cell.

10. The host cell of claim 5, wherein the host cell is a plant cell.

* * * * *